(12) United States Patent
Carpenter et al.

(10) Patent No.: US 8,545,754 B2
(45) Date of Patent: Oct. 1, 2013

(54) RADIAL DESIGN OXYGENATOR WITH HEAT EXCHANGER

(75) Inventors: Walt L. Carpenter, Minneapolis, MN (US); Robert W. Olsen, Plymouth, MN (US); Michael J. Hobday, Lino Lakes, MN (US); Alford L. McLevish, Maple Grove, MN (US); Christopher J. Plott, St. Paul, MN (US); Roderick E. Briscoe, Rogers, MN (US); Patrick J. Cloutier, Andover, MN (US); Anil Thapa, Blaine, MN (US); Ming Li, Roseville, MN (US); Kevin McIntosh, Brooklyn Park, MN (US); Ken Merte, Southlake, TX (US)

(73) Assignee: Medtronic, Inc., Minneapolis, MN (US)

( * ) Notice: Subject to any disclaimer, the term of this patent is extended or adjusted under 35 U.S.C. 154(b) by 541 days.

(21) Appl. No.: 12/428,674

(22) Filed: Apr. 23, 2009

(65) Prior Publication Data

US 2010/0274170 A1  Oct. 28, 2010

(51) Int. Cl.
*A61M 1/00* (2006.01)
*A61M 1/16* (2006.01)

(52) U.S. Cl.
CPC .................................. *A61M 1/1698* (2013.01)
USPC .................. 422/46; 422/44; 422/45; 422/48; 604/4.01; 604/6.09; 604/6.13; 604/6.14

(58) Field of Classification Search
USPC ..................... 604/4.01, 5.01, 6.09, 6.13, 6.14; 422/44, 45, 46, 48
See application file for complete search history.

(56) References Cited

U.S. PATENT DOCUMENTS

| | | | |
|---|---|---|---|
| 3,342,729 | A | 9/1967 | Strand |
| 3,422,008 | A | 1/1969 | McLain |
| 3,455,460 | A | 7/1969 | Mahon |
| 3,526,011 | A | 9/1970 | Smith |
| 3,536,611 | A | 10/1970 | deFilippi |
| 3,557,962 | A | 1/1971 | Kohl |

(Continued)

FOREIGN PATENT DOCUMENTS

| | | |
|---|---|---|
| EP | 1 834 656 | 9/2007 |
| WO | 96/00593 | 1/1996 |

(Continued)

OTHER PUBLICATIONS

Groom, et al., "Pediatric Cardiopulmonary Bypass: A Review of Current Practice," Internat. Anesth. Clinics, 1996, 34(2), pp. 141-164.

(Continued)

*Primary Examiner* — Leslie Deak

(57) ABSTRACT

Disclosed is an apparatus for oxygenating and controlling the temperature of blood in an extracorporeal circuit. The apparatus has an inlet and an outlet that is located radially outward from the inlet in order to define a flowpath through the apparatus. The apparatus comprises: a core that is substantially centrally located in the apparatus and to which blood from a patient can be supplied through the inlet; a heat exchanger comprising a plurality of heat transfer elements that are arranged around the core and between which blood from the core can move radially outward; and an oxygenator comprising a plurality of gas exchange elements that are arranged around the heat exchanger and between which blood from the heat exchanger can move radially outward before exiting the apparatus through the outlet.

40 Claims, 18 Drawing Sheets

(56) References Cited

U.S. PATENT DOCUMENTS

| | | |
|---|---|---|
| 3,755,034 A | 8/1973 | Mahon |
| 3,794,468 A | 2/1974 | Leonard |
| 3,801,401 A | 4/1974 | Cope |
| 3,884,424 A | 5/1975 | Bosquain |
| 3,993,816 A | 11/1976 | Baudet |
| 4,020,230 A | 4/1977 | Mahoney |
| 4,045,851 A | 9/1977 | Ashare |
| 4,101,423 A | 7/1978 | Merrill |
| 4,137,394 A | 1/1979 | Meihuizen |
| 4,140,637 A | 2/1979 | Walter |
| 4,172,794 A | 10/1979 | Sigdell |
| 4,224,094 A | 9/1980 | Amicel |
| 4,224,164 A | 9/1980 | Brauer |
| 4,231,425 A | 11/1980 | Engstrom |
| 4,231,988 A | 11/1980 | Kurata |
| 4,239,729 A | 12/1980 | Hasegawa |
| 4,268,279 A | 5/1981 | Shindo |
| 4,328,102 A | 5/1982 | Belhouse |
| 4,336,138 A | 6/1982 | Taniyama |
| 4,352,736 A | 10/1982 | Ukai |
| 4,356,138 A | 10/1982 | Kavesh |
| 4,368,124 A | 1/1983 | Brumfield |
| 4,374,802 A | 2/1983 | Fukasawa |
| 4,376,095 A | 3/1983 | Hasegawa |
| 4,389,363 A | 6/1983 | Molthop |
| 4,413,110 A | 11/1983 | Kavesh |
| 4,424,190 A | 1/1984 | Mather |
| 4,430,219 A | 2/1984 | Kuzumoto |
| 4,451,562 A | 5/1984 | Elgas |
| 4,469,659 A | 9/1984 | Carson |
| 4,529,139 A | 7/1985 | Smith |
| 4,556,489 A | 12/1985 | Dietrrich, Jr. |
| 4,559,999 A | 12/1985 | Servas |
| 4,572,446 A | 2/1986 | Leonard |
| 4,622,206 A | 11/1986 | Torgeson |
| 4,631,128 A | 12/1986 | Coplan |
| 4,639,353 A | 1/1987 | Takemura |
| 4,645,645 A | 2/1987 | Martinez |
| 4,657,743 A | 4/1987 | Kanno |
| 4,659,549 A | 4/1987 | Hamada |
| 4,662,573 A | 5/1987 | Camadella |
| 4,663,125 A | 5/1987 | Gordon |
| 4,689,255 A | 8/1987 | Smoot |
| 4,690,758 A | 9/1987 | Leonard |
| 4,698,207 A | 10/1987 | Bringham |
| 4,708,796 A | 11/1987 | Yoshimoto |
| 4,715,953 A | 12/1987 | Leonard |
| 4,719,277 A | 1/1988 | Behnke |
| 4,722,829 A | 2/1988 | Giter |
| 4,725,017 A | 2/1988 | Camardella |
| 4,735,775 A | 4/1988 | Leonard |
| 4,746,075 A | 5/1988 | Hoxit |
| 4,749,551 A | 6/1988 | Borgione |
| 4,761,864 A | 8/1988 | Berger |
| 4,781,889 A | 11/1988 | Fukasawa |
| 4,791,054 A | 12/1988 | Hamada |
| 4,808,378 A | 2/1989 | Nakanishi |
| 4,818,490 A | 4/1989 | Carson |
| 4,824,566 A | 4/1989 | Thibos |
| 4,838,970 A | 6/1989 | Thibos |
| 4,863,600 A | 9/1989 | Leonard |
| 4,876,066 A | 10/1989 | Bringham |
| 4,902,476 A | 2/1990 | Gordon |
| 4,906,581 A | 3/1990 | Baker |
| 4,909,989 A | 3/1990 | Fukazawa |
| 4,911,846 A | 3/1990 | Akasu |
| 4,923,679 A | 5/1990 | Fukasawa |
| 4,940,617 A | 7/1990 | Baurmeister |
| 4,948,444 A | 8/1990 | Schutz |
| 4,948,560 A | 8/1990 | Deguchi |
| 4,952,312 A | 8/1990 | Zantonelli |
| 4,954,317 A | 9/1990 | Raible |
| 4,971,836 A | 11/1990 | Fukasawa |
| 4,975,247 A | 12/1990 | Badolato et al. |
| 5,034,188 A | 7/1991 | Nakanishi |
| 5,037,610 A | 8/1991 | Fukasawa |
| 5,039,482 A | 8/1991 | Panzani |
| 5,043,140 A | 8/1991 | Combs |
| 5,055,753 A | 10/1991 | Hermanson |
| 5,058,661 A | 10/1991 | Oshiyama |
| 5,117,903 A | 6/1992 | Oshiyama et al. |
| 5,120,501 A | 6/1992 | Mathewson et al. |
| 5,124,127 A | 6/1992 | Jones et al. |
| 5,135,804 A | 8/1992 | Harpell |
| 5,137,531 A | 8/1992 | Lee |
| 5,141,031 A | 8/1992 | Baurmeister |
| 5,143,312 A | 9/1992 | Baurmeister |
| 5,152,964 A | 10/1992 | Leonard |
| 5,162,101 A | 11/1992 | Cosentino |
| 5,162,102 A | 11/1992 | Nogawa et al. |
| 5,186,713 A | 2/1993 | Raible |
| 5,186,832 A | 2/1993 | Mancusi |
| 5,217,689 A | 6/1993 | Raible |
| 5,224,522 A | 7/1993 | Baurmeister |
| 5,225,131 A | 7/1993 | Tamaru et al. |
| 5,225,161 A | 7/1993 | Mathewson et al. |
| 5,230,862 A | 7/1993 | Berry |
| 5,234,663 A | 8/1993 | Jones |
| 5,236,665 A | 8/1993 | Mathewson |
| 5,240,677 A | 8/1993 | Jones |
| 5,244,930 A | 9/1993 | Trudell |
| 5,263,924 A | 11/1993 | Mathewson |
| 5,270,004 A | 12/1993 | Cosentino |
| 5,270,005 A | 12/1993 | Raible |
| 5,284,584 A | 2/1994 | Huang |
| 5,294,397 A | 3/1994 | Oshiyama et al. |
| 5,294,401 A | 3/1994 | Hagiwara |
| 5,297,591 A | 3/1994 | Baurmeister |
| 5,299,749 A | 4/1994 | Thorogood |
| 5,312,589 A | 5/1994 | Reeder |
| 5,316,724 A | 5/1994 | Mathewson |
| 5,338,512 A | 8/1994 | Mathewson et al. |
| 5,346,621 A | 9/1994 | Haworth et al. |
| 5,352,361 A | 10/1994 | Prasad |
| 5,354,470 A | 10/1994 | Seita et al. |
| 5,358,689 A | 10/1994 | Jones et al. |
| 5,376,334 A | 12/1994 | Haworth et al. |
| 5,382,407 A | 1/1995 | Leonard |
| 5,395,468 A | 3/1995 | Juliar et al. |
| 5,411,705 A | 5/1995 | Thor et al. |
| 5,421,405 A | 6/1995 | Goodin et al. |
| 5,429,184 A | 7/1995 | Bach et al. |
| 5,429,486 A | 7/1995 | Schock |
| 5,429,802 A | 7/1995 | Hagiwara |
| 5,449,430 A | 9/1995 | Porta |
| 5,462,619 A | 10/1995 | Haworth et al. |
| 5,468,449 A | 11/1995 | Sjogren |
| 5,470,531 A | 11/1995 | Sjogren |
| 5,474,740 A | 12/1995 | Trudell |
| 5,489,382 A | 2/1996 | Tatebe et al. |
| 5,489,413 A | 2/1996 | Carson |
| 5,514,335 A | 5/1996 | Leonard |
| 5,540,653 A | 7/1996 | Schock |
| 5,552,047 A | 9/1996 | Oshida et al. |
| 5,578,267 A * | 11/1996 | Cosentino et al. .............. 422/46 |
| 5,580,522 A | 12/1996 | Leonard |
| 5,582,794 A | 12/1996 | Hagiwara |
| 5,591,399 A | 1/1997 | Goldman |
| 5,601,714 A | 2/1997 | Haveland |
| 5,634,892 A | 6/1997 | Wahlen |
| 5,651,765 A | 7/1997 | Haworth et al. |
| 5,674,452 A | 10/1997 | Carson |
| 5,682,877 A | 11/1997 | Mondry |
| 5,695,717 A | 12/1997 | Polaschegg |
| 5,706,889 A | 1/1998 | Bach et al. |
| 5,718,869 A | 2/1998 | Bach et al. |
| 5,718,871 A | 2/1998 | Elgas |
| 5,733,398 A | 3/1998 | Carson et al. |
| 5,741,424 A | 4/1998 | Plunkett |
| 5,746,575 A | 5/1998 | Westphal et al. |
| 5,747,138 A | 5/1998 | Leonard |
| 5,762,868 A | 6/1998 | Leonard |
| 5,762,869 A | 6/1998 | White et al. |
| 5,762,870 A | 6/1998 | Vallana |

| | | |
|---|---|---|
| 5,762,875 A | 6/1998 | Gremel |
| 5,766,480 A | 6/1998 | Cosentino et al. |
| 5,770,149 A | 6/1998 | Raible et al. |
| 5,817,278 A | 10/1998 | Fini |
| 5,817,279 A | 10/1998 | Eilers et al. |
| 5,823,987 A * | 10/1998 | Elgas et al. ............... 604/6.13 |
| 5,830,370 A | 11/1998 | Maloney, Jr. et al. |
| 5,855,201 A | 1/1999 | Fukui |
| 5,858,233 A | 1/1999 | Elgas et al. |
| 5,863,179 A | 1/1999 | Westphal et al. |
| RE36,125 E | 3/1999 | Haworth et al. |
| 5,876,667 A | 3/1999 | Gremel et al. |
| 5,888,611 A | 3/1999 | Leonard |
| 5,900,142 A | 5/1999 | Maloney |
| 5,906,741 A | 5/1999 | Elgas et al. |
| 5,997,816 A | 12/1999 | McIntosh et al. |
| 6,001,288 A | 12/1999 | Saruhashi et al. |
| RE36,774 E | 7/2000 | Cosentino et al. |
| 6,113,782 A * | 9/2000 | Leonard ............... 210/321.89 |
| 6,210,365 B1 | 4/2001 | Afzal |
| 6,224,819 B1 | 5/2001 | Kim et al. |
| 6,273,355 B1 | 8/2001 | Van Driel |
| 6,302,860 B1 | 10/2001 | Gremel et al. |
| 6,368,557 B1 | 4/2002 | Piplani et al. |
| 6,379,618 B1 | 4/2002 | Piplani et al. |
| 6,387,323 B1 | 5/2002 | Afzal et al. |
| 6,423,269 B1 | 7/2002 | Gremel |
| 6,428,747 B1 | 8/2002 | Dueri et al. |
| 6,454,999 B1 | 9/2002 | Farhangnia et al. |
| 6,495,101 B1 | 12/2002 | Yokoyama |
| 6,497,841 B1 | 12/2002 | Plotkin et al. |
| 6,503,450 B1 | 1/2003 | Afzal et al. |
| 6,503,451 B2 | 1/2003 | Ikeda et al. |
| 6,508,983 B1 | 1/2003 | McBurney |
| 6,613,279 B1 | 9/2003 | Elgas et al. |
| 6,613,281 B2 | 9/2003 | Filho et al. |
| 6,638,479 B1 | 10/2003 | Elgas et al. |
| 6,682,698 B2 | 1/2004 | Chambers et al. |
| 6,689,315 B2 | 2/2004 | Linker et al. |
| 6,723,283 B2 | 4/2004 | Ghelli |
| 6,730,267 B2 | 5/2004 | Stringer et al. |
| 6,773,670 B2 | 8/2004 | Stringer et al. |
| 6,852,280 B2 | 2/2005 | Vijay et al. |
| 6,890,316 B2 | 5/2005 | Rawles et al. |
| 6,946,099 B2 | 9/2005 | Vijay et al. |
| 6,960,322 B2 | 11/2005 | Stringer et al. |
| 6,960,332 B2 | 11/2005 | Erga |
| 6,994,824 B2 | 2/2006 | Mochizuki et al. |
| 6,998,093 B1 | 2/2006 | McIntosh |
| 7,022,099 B2 | 4/2006 | Litzie et al. |
| 7,022,284 B2 | 4/2006 | Brian et al. |
| 7,238,320 B2 | 7/2007 | Ghelli et al. |
| 7,291,124 B2 | 11/2007 | Rawles et al. |
| 7,431,754 B2 | 10/2008 | Ogihara et al. |
| 7,476,359 B2 | 1/2009 | Maianti et al. |
| 7,541,000 B2 | 6/2009 | Stringer et al. |
| 7,749,435 B2 | 7/2010 | Ogihara et al. |
| 2004/0219060 A1 | 11/2004 | Maianti et al. |
| 2007/0166189 A1 | 7/2007 | Ogihara |
| 2007/0217948 A1 | 9/2007 | Ghelli et al. |
| 2007/0231203 A1 | 10/2007 | Mimzoguchi et al. |
| 2009/0087342 A1 | 4/2009 | Maianti et al. |
| 2009/0107898 A1 | 4/2009 | Ogihara et al. |

FOREIGN PATENT DOCUMENTS

| | | |
|---|---|---|
| WO | 97/26029 | 7/1997 |
| WO | 97/26030 | 7/1997 |
| WO | 97/26032 | 7/1997 |
| WO | 97/26033 | 7/1997 |
| WO | 97/33636 | 9/1997 |

OTHER PUBLICATIONS

Groom, et al., "Paediatric perfusion practice in North America: an update," Perfusion, 1995;10:393-401.

* cited by examiner

RADIAL DESIGN OXYGENATOR WITH HEAT EXCHANGER

FIELD OF THE INVENTION

The invention generally relates to cardiopulmonary bypass circuits, and particularly to an apparatus that includes a heat exchanger, an oxygenator, a core, and an optional pump that may be arranged around each other. For example, one embodiment of the apparatus includes a core, a heat exchanger arranged about the core, an oxygenator arranged about the heat exchanger, to which blood is delivered into the core, that optionally comprises a pump, and through which blood moves radially outward from the apparatus, with a fluid medium being supplied separately to the heat exchanger and a gas medium being supplied separately to the oxygenator in directions generally transverse to the radial movement of the blood.

BACKGROUND OF THE INVENTION

A cardiopulmonary bypass circuit (i.e., a heart-lung bypass machine) mechanically pumps a patient's blood and oxygenates the blood during major surgery. Blood oxygenators are disposable components of heart-lung bypass machines used to oxygenate blood. A typical commercially available blood oxygenator integrates a heat exchanger with a membrane-type oxygenator.

Typically, in a blood oxygenator, a patient's blood is continuously pumped through the heat exchanger portion prior to the oxygenator portion. A suitable heat transfer fluid, such as water, is pumped through the heat exchanger, separate from the blood but in heat transfer relationship therewith. The water is either heated or cooled externally of the heat exchanger. The heat exchanger is generally made of a metal or a plastic, which is able to transfer heat effectively to blood coming into contact with the metal or plastic. After blood contacts the heat exchanger, the blood then typically flows into the oxygenator.

The oxygenator generally comprises a so-called "bundle" of thousands of tiny hollow fibers typically made of a special polymeric material having microscopic pores. The blood exiting the heat exchanger then flows around the outside surfaces of the fibers of the oxygenator. At the same time, an oxygen-rich gas mixture, sometimes including anesthetic agents, flows through the hollow fibers. Due to the relatively high concentration of carbon dioxide in the blood arriving from the patient, carbon dioxide from the blood diffuses through the microscopic pores in the fibers and into the gas mixture. Due to the relatively low concentration of oxygen in the blood arriving from the patient, oxygen from the gas mixture in the fibers diffuses through the microscopic pores and into the blood. The oxygen content of the blood is thereby raised, and its carbon dioxide content is reduced.

An oxygenator must have a sufficient volumetric flow rate to allow proper temperature control and oxygenation of blood. A disadvantage of perfusion devices incorporating such oxygenators is that the priming volume of blood is large. Having such a large volume of blood outside of the patient's body at one time acts to dilute the patient's own blood supply. Thus, the need for a high prime volume of blood in an oxygenator is contrary to the best interest of the patient who is undergoing surgery and is in need of a maximum possible amount of fully oxygenated blood in his or her body at any given time. This is especially true for small adult, pediatric and infant patients. As such, hemoconcentration of the patient and a significant amount of additional blood, or both, may be required to support the patient. Therefore, it is desirable to minimize the prime volume of blood necessary within the extracorporeal circuit, and preferably to less than 500 cubic centimeters. One way to minimize the prime volume is to reduce the volume of the blood oxygenator. There are limits to how small the oxygenator can be made, however, because of the need for adequate oxygen transfer to the blood, which depends in part on a sufficient blood/membrane interface area.

The cells (e.g., red blood cells, white blood cells, platelets) in human blood are delicate and can be traumatized if subjected to shear forces. Therefore, the blood flow velocity inside a blood oxygenator must not be excessive. The configuration and geometry, along with required velocities of the blood make some perfusion devices traumatic to the blood and unsafe. In addition, the devices may create re-circulations (eddies) or stagnant areas that can lead to clotting. Thus, the configuration and geometry of the inlet port, manifolds and outlet port for a blood flow path is desired to not create re-circulations (eddies), while also eliminating stagnant areas that can lead to blood clot production.

Overall, there is a need for improved components of cardiopulmonary bypass circuits. Such improved components will preferably address earlier problematic design issues, as well as be effective at oxygenating and controlling the temperature of blood.

SUMMARY OF THE INVENTION

The present invention overcomes the shortcomings of the prior art by providing an apparatus that is part of a cardiopulmonary bypass circuit and that oxygenates and controls the temperature of blood external to a patient using a design that allows blood to flow radially and sequentially through a heat exchanger and an oxygenator. The heat exchanger can be arranged around (e.g., concentrically about) a core and the oxygenator around (e.g., concentrically arranged about) the heat exchanger, or vice versa. Blood is delivered in a core, that optionally comprises a pump, and moves radially outward through both the heat exchanger and oxygenator. A heat transfer medium is preferably supplied separately to the heat exchanger and an oxygen-containing gas medium is supplied separately to the oxygenator, with both media being supplied in directions generally transverse to the radial movement of the blood through the apparatus.

One advantage of the radial movement of blood through both the heat exchanger and the oxygenator in the apparatus is that it increases the overall performance and efficiency of the apparatus. The radial design provides optimal distribution of blood over surface area used for gas and heat exchange. The radial flow also results in a low pressure drop within the apparatus.

For embodiments of the invention in which the oxygenator is located around or downstream from the heat exchanger, the arrangement is more efficient. Since gas solubility varies significantly with temperature, it is important that blood be oxygenated at the temperature at which it will enter the body. Heating the blood before oxygenating the blood, therefore, is more efficient.

Another advantage of the invention is that the apparatus is safer to use for a patient. The radial blood flow through both the heat exchanger and oxygenator, decreases recirculation of blood or stagnant areas of blood, which reduces the chance of blood clots. In addition, the radial flow minimizes shear forces that would otherwise traumatize blood cells.

Another advantage of the apparatus is that the design eliminates certain components necessary in prior art devices, which in turn reduces the prime volume of blood necessary for the apparatus. The benefit of reducing prime volume is that a patient undergoing blood oxygenation is able to maintain a maximum possible amount of fully oxygenated blood in his or her body at any given time during surgery. This is especially important for small adult, pediatric and infant patients.

The apparatus also has improved manufacturability over other such apparatuses. The invention includes fewer necessary parts than other similar devices, which makes the apparatus easier and cheaper to manufacture.

An embodiment of the invention is an apparatus for oxygenating and controlling the temperature of blood in an extracorporeal circuit. The apparatus has an inlet and an outlet that is located radially outward from the inlet in order to define a flowpath through the apparatus. The apparatus comprises: a core that is substantially centrally located in the apparatus and to which blood from a patient can be supplied through the inlet; a heat exchanger comprising a plurality of heat transfer elements that are arranged around the core and between which blood from the core can move radially outward; and an oxygenator comprising a plurality of gas exchange elements that are arranged around the heat exchanger and between which blood from the heat exchanger can move radially outward before exiting the apparatus through the outlet.

In the embodiment described above, the plurality of heat transfer elements may be arranged concentrically about the core. The plurality of gas exchange elements may be arranged concentrically about the heat exchanger. The core may comprise a lumen having a longitudinal axis and a plurality of openings through which blood can move radially outward to the heat exchanger. The blood can move axially along the lumen of the core until reaching the plurality of openings and then can move radially outward through the plurality of openings in a substantially transverse direction to the longitudinal axis. The blood can move radially outward from the core through substantially all of 360 degrees around the longitudinal axis. The plurality of heat transfer elements may include a lumen to which a fluid medium can be supplied in order to control the temperature of blood that can move between the plurality of heat transfer elements. The plurality of heat transfer elements may be arranged such that movement of the fluid medium through the plurality of heat transfer elements is substantially transverse to the radially outward direction that blood can move between the plurality of heat transfer elements. The plurality of gas exchange elements may comprise a lumen through which an oxygen-containing gas medium may be supplied in order to oxygenate blood that can move between the plurality of gas exchange elements. The plurality of gas exchange elements may be arranged such that the movement of the gas medium through the plurality of gas exchange elements is substantially transverse to the radially outward direction that blood can move between the plurality of gas exchange elements. The apparatus may further comprise a filter that is arranged around the oxygenator and through which blood moving radially outward from the oxygenator can move before exiting the apparatus through the outlet. The core may comprise a longitudinal axis and blood may move radially outward from the oxygenator to the filter through substantially all of 360 degrees around the longitudinal axis. The apparatus may further comprise a housing that retains the core, the heat exchanger and the oxygenator. The housing may include the inlet, which is in communication with the core, and may include the outlet, which is located radially outward from the oxygenator. The plurality of heat transfer elements may be wound on the core, and the plurality of gas exchange elements may be wound on the heat exchanger. The apparatus may further comprise a filter including filter media, wherein the filter media may be wound in between the plurality of gas exchange elements. The apparatus may further comprise a filter through which blood can move before exiting the apparatus through the outlet. The core may comprise a longitudinal axis and blood may move radially outward from the heat exchanger through substantially all of 360 degrees around the longitudinal axis. The apparatus may further comprise a filter that is arranged between the heat exchanger and the oxygenator. The apparatus may further comprise a filter including filter media, wherein at least a portion of the filter media of the filter is located within the oxygenator.

Another embodiment of the invention is an apparatus for oxygenating and controlling the temperature of blood in an extracorporeal circuit. The apparatus has an inlet and an outlet that is located radially outward from the inlet in order to define a flowpath through the apparatus. The apparatus comprises: a core that is substantially centrally located in the apparatus and to which blood from a patient can be supplied through the inlet; a heat exchanger comprising a plurality of heat transfer elements that are arranged around the core such that blood can move radially outward through the heat exchanger; and an oxygenator comprising a plurality of gas exchange elements that are arranged around the heat exchanger such that blood can move from the heat exchanger to the oxygenator without structural obstruction and radially outward through the oxygenator before exiting the apparatus through the outlet.

In the embodiment described above, the plurality of heat transfer elements may be arranged concentrically about the core. The plurality of gas exchange elements may be arranged concentrically about the heat exchanger. Blood may move from the core to the heat exchanger without structural obstruction. The core may include a lumen having a longitudinal axis and a plurality of openings through which blood can move radially outward to the heat exchanger. Blood may move axially along the lumen of the core until reaching the plurality of openings and then may move radially outward through the plurality of openings in a substantially transverse direction to the longitudinal axis. Blood may move radially outward through substantially all of 360 degrees around the longitudinal axis of the core. The plurality of heat transfer elements may include a lumen through which a fluid medium can be supplied in order to control the temperature of blood that can move between the plurality of heat transfer elements. The plurality of heat transfer elements may be arranged such that movement of the fluid medium through the plurality of heat transfer elements is substantially transverse to the radially outward direction that blood can move between the plurality of heat transfer elements. The plurality of gas exchange elements may include a lumen through which an oxygen-containing gas medium can be supplied in order to oxygenate blood that can move between the plurality of gas exchange elements. The plurality of gas exchange elements may be arranged such that the movement of the gas medium through the plurality of gas exchange elements is substantially transverse to the radially outward direction that blood can move between the plurality of gas exchange elements. The apparatus may further comprise a filter that is concentrically arranged about the oxygenator and through which blood moving radially outward from the oxygenator can move before exiting the apparatus through the outlet. The core may comprise a longitudinal axis and blood may move radially outward from the oxygenator through substantially all of 360 degrees around the longitudinal axis. The apparatus may further comprise a housing that retains the core, the heat exchanger and the oxygenator. The housing may include the inlet, which is in communication with the core. The housing may include the outlet, which is located radially outward from the oxygenator. The plurality of heat transfer elements may be wound on the core. The plurality of gas exchange elements may be wound on the heat exchanger. The apparatus may further comprise a filter including filter media, wherein the filter media is wound in between the plurality of gas exchange elements. The apparatus may further comprise a filter through which blood can move before exiting the apparatus through the outlet. The core may comprise a longitudinal axis and blood may move radially outward from the heat exchanger through substantially all of 360 degrees around the longitudinal axis. The apparatus may further comprise a fitter that is arranged between the heat exchanger and the oxygenator. The apparatus may further comprise a filter including filter media, wherein at least a portion of the filter media of the filter is located within the oxygenator.

BRIEF DESCRIPTION OF THE DRAWINGS

The invention will be further explained with reference to the appended Figures, wherein like structure is referred to by like numerals throughout the several views, and wherein.

DETAILED DESCRIPTION OF THE INVENTION

Figure 1:
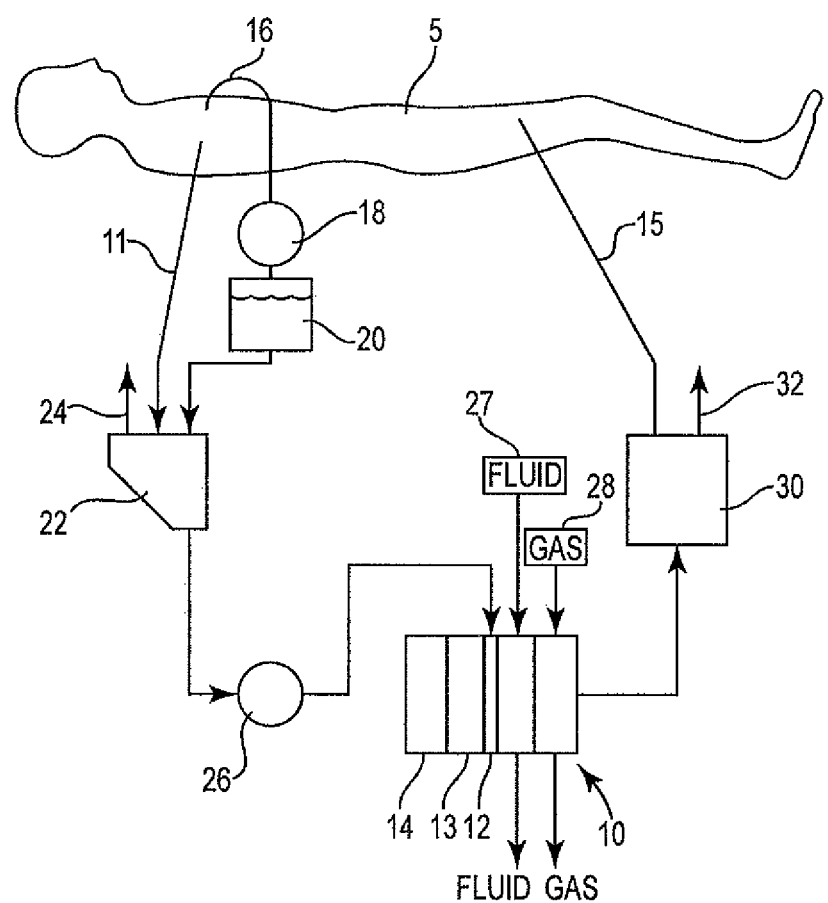
FIG. 1 is a schematic drawing of a cardiopulmonary bypass circuit including an apparatus in accordance with the invention.

Referring to FIG. 1, an exemplary cardiopulmonary bypass circuit is schematically illustrated, which includes an embodiment of an apparatus 10 in accordance with the invention. The circuit generally draws blood of a patient 5 during cardiovascular surgery through a venous line 11, oxygenates the blood, and returns the oxygenated blood to the patient 5 through an arterial line 15. Venous blood drawn from the patient through line 11 is discharged into a venous reservoir 22. Cardiotomy blood and surgical field debris are aspirated by a suction device 16 and are pumped by pump 18 into a cardiotomy reservoir 20. Once defoamed and filtered, the cardiotomy blood is also discharged into venous reservoir 22. Alternatively, the function of the cardiotomy reservoir 20 may be integrated into the venous reservoir 22. In the venous reservoir 22, air entrapped in the venous blood rises to the surface of the blood and is vented to the atmosphere through a purge line 24.

A pump 26 draws blood from the venous reservoir 22 and pumps it through the apparatus 10 of the invention. Some exemplary types of pumps 26 include, but are not limited to, roller pumps and centrifugal pumps, for example. The pump 26 may be external to the apparatus 10, as shown, or may alternatively be incorporated into a core 12 of the apparatus 10. As another alternative, the pump 26 could be located in the circuit after the apparatus 10 and act to pull blood through the apparatus 10 (i.e., use negative pressure) rather than pump or push blood (i.e., use positive pressure) through the apparatus 10. As shown in the embodiment, the pump 26 is external and pumps blood into the core 12 of the apparatus 10. As another alternative, more than one pump may be used.

In the apparatus 10, the core 12 is preferably configured such that blood is able to flow radially outward from the core 12 to a heat exchanger 13, preferably comprising a plurality of heat transfer elements (not shown), that are located around the core 12. The plurality of heat transfer elements may be concentrically arranged about the core 12. The plurality of heat transfer elements may be directly wound on the core 12, or may be wound or placed such that a space results between the heat exchanger 13 and core 12. Preferably, there is minimal or no structural obstruction to blood flow between the core 12 and heat exchanger 13.

A heat transfer medium is supplied by a fluid supply 27 to the plurality of heat transfer elements and removed as indicated schematically. The fluid medium is preferably heated or cooled separately in the fluid supply 27 and is provided to the plurality of heat transfer elements in order to control the temperature of the blood flowing radially outward from the core 12 and between the heat transfer elements. Alternatively, the heat transfer medium may not be a fluid, but could be thermal energy that is conducted through the heat transfer elements in order to heat the blood.

Next, the blood moves radially outward from the heat exchanger 13 to an adjacent oxygenator 14, preferably comprising a plurality of gas exchange elements (not shown), that are located around the heat exchanger 13. The plurality of gas exchange elements may be concentrically arranged about the heat exchanger 13. The plurality of gas exchange elements may be wound directly on the heat exchanger 13, or may be wound or placed such that a space or void results between the heat exchanger 13 and the oxygenator 14. Preferably, there is minimal or no structural obstruction to blood flow between the heat exchanger 13 and the oxygenator 14.

The oxygenator 14 is preferably a membrane oxygenator, and most preferably a hollow fiber oxygenator. Thus, the gas exchange elements are preferably fibers, although other such elements are also contemplated. An oxygen-containing gas medium is preferably supplied by gas supply 28 to lumens of the gas exchange elements and removed, as shown schematically. The oxygen-containing gas medium is provided to the oxygenator 14 in order to deliver oxygen to the blood flowing radially between the plurality of heat exchange elements, as well as to remove carbon dioxide.

The fluid and gas media and the blood moving through the apparatus 10 are preferably compartmentalized or kept separate, so as to not allow mixing, which would decrease the effectiveness and efficiency of the apparatus 10. The direction of movement of the fluid and gas media through the heat exchanger 13 and oxygenator 14 of the apparatus 10 are preferably generally transverse to the direction of radial blood flow through the apparatus 10.

Oxygenated and temperature-controlled blood is collected after moving out of the oxygenator 14 of the apparatus 10, and preferably flows to an arterial filter 30 and then into the arterial line 15. The arterial filter 30 preferably traps air bubbles in the blood that are larger than about 20-40 micrometers where the bubbles can be removed through a purge line 32. As an alternative of the invention, the apparatus 10 itself may include a filter, with such filter being preferably located around the oxygenator 14, although other locations are also contemplated by the invention, as described herein below.

The circuit shown in FIG. 1 is exemplary, and it should be understood that the apparatus 10 of the invention may be incorporated into any suitable cardiopulmonary bypass circuit or other suitable extracorporeal system, for example.

Figure 2:
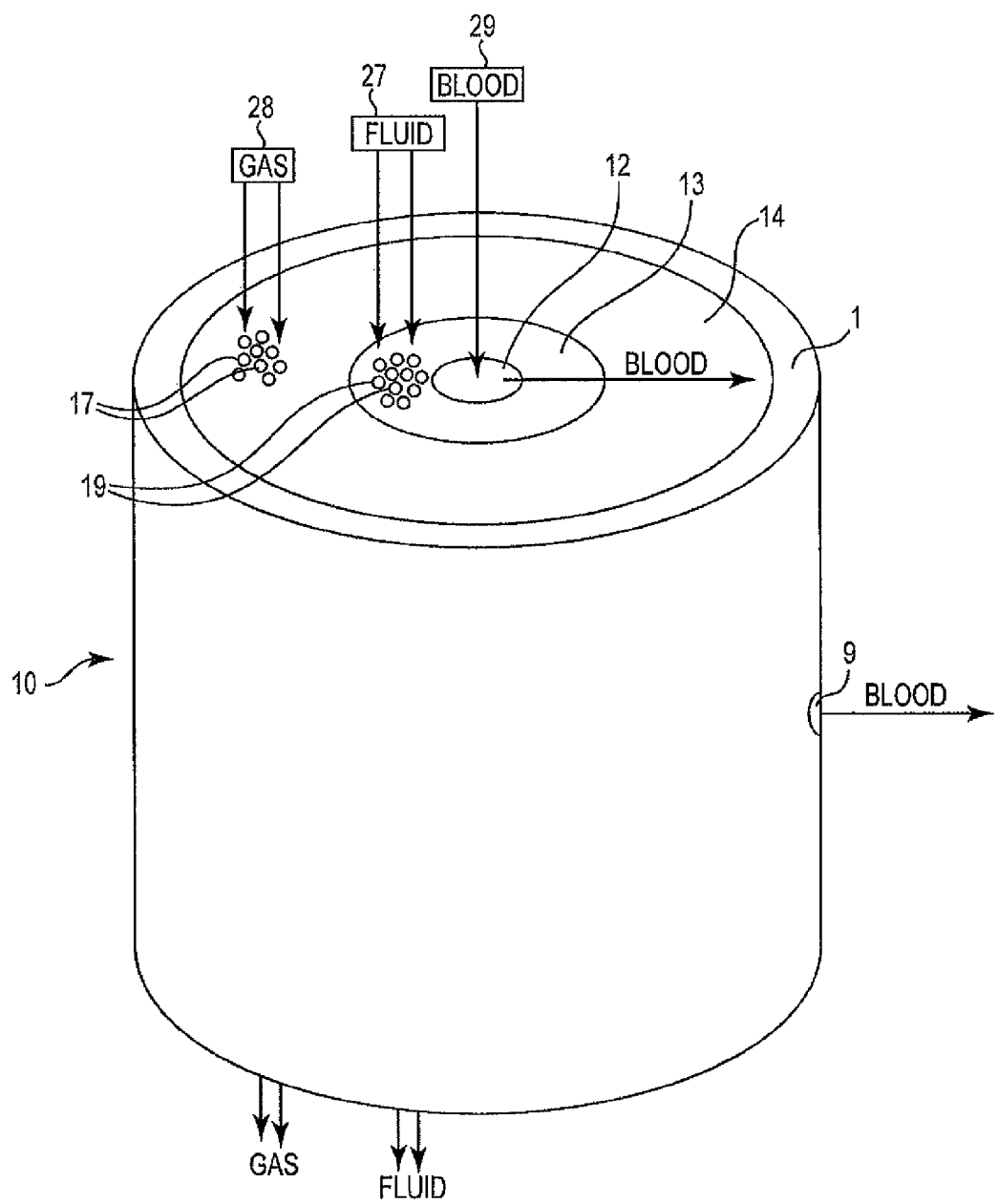
FIG. 2 is a schematic drawing of an apparatus, in accordance with the invention, showing blood, fluid medium and gas medium flow through the apparatus.

FIG. 2 is a schematic, perspective view of the apparatus 10 of the invention with flow of blood through the apparatus 10 and flow of fluid medium and gas medium into and out of the apparatus 10 indicated by arrows labeled as such. Blood from a patient enters the core 12 from a blood supply 29 (e.g., a venous reservoir) either by being pumped into the core 12 or pulled into the core 12 by an external pump (not shown). The pump may optionally be located in the core 12. The blood then sequentially moves radially outward from the core 12 into the heat exchanger 13 that is located around, and preferably arranged concentrically about, the core 12. Preferably, the blood moves continuously radially outward through substantially all of 360 degrees around the core 12 and evenly along substantially all of the length of the core 12. Sequentially, the blood moves radially outward from the heat exchanger 13 to and through the oxygenator 14 that is located around, and preferably arranged concentrically about, the heat exchanger 13. Preferably, the blood moves continuously radially outward through substantially all of 360 degrees around the heat exchanger 13 and the oxygenator 14. The oxygenated and temperature-controlled blood is then collected and exits the apparatus 10 preferably from an outlet port 9 in apparatus 10, and is returned to the patient through an arterial line (not shown). The apparatus 10 may include a housing, such as housing 1, upon which the blood is collected, for example on an inner surface thereof (not shown), and through which blood is allowed to exit the apparatus 10 through outlet 9.

Blood circulated through apparatus 10, for example, is preferably filtered before being returned to the patient, in order to remove air bubbles. Alternatively, the apparatus 10 may include a filter that could be concentrically arranged about the heat exchanger 13 and/or the oxygenator 14 and through which oxygenated blood would flow radially outward before being collected and returned to the patient. The filter could also be wound around a partially complete oxygenator, with remaining gas exchange elements (e.g., fibers) of the oxygenator being wound on top of the filter.

The heat transfer medium that is supplied to the heat exchanger 13 from a fluid medium supply 27 is heated or cooled externally to the apparatus 10. The fluid medium is supplied to lumens in a plurality of heat transfer elements 17 (only several of which are illustrated in FIG. 2) that comprise the heat exchanger 13. The heat transfer elements 17 conduct heat and either heat or cool the blood as the blood moves radially through the heat transfer elements 17 of the heat exchanger 13.

The gas medium that is supplied to the oxygenator 14 contains oxygen. The gas medium is delivered to lumens in a plurality of gas exchange elements 19 (only several of which are illustrated in FIG. 2) that comprise the oxygenator 14. The gas exchange elements 19 are preferably hollow fibers that are microporous in nature, which allows oxygen in the fibers 19 to diffuse through micropores into blood flowing between the fibers 19 and also allows carbon dioxide to diffuse from the blood into the gas medium in the fibers 19 and be removed from the blood.

The purpose of the radial design of the apparatus 10 is to allow for substantially continuous radial flow of blood through the apparatus 10. The radial flow design is beneficial because it optimizes distribution of the blood to the surface area for heat and oxygen exchange, which makes the design more efficient. Also, substantially continuous radial flow decreases the recirculation of blood and stagnant areas of blood with the apparatus, which decreases the chances of blood clotting. In addition, the design decreases shear forces on the blood, which can cause damage to blood cells. The radial design also decreases the prime volume of blood necessary compared to other such devices, which is beneficial for smaller patients, including children and small adults.

In order for the apparatus 10 to work efficiently, the gas medium, fluid medium and blood are compartmentalized or separated in the apparatus 10. Later embodiments of the apparatus of the invention described below demonstrate how the gas medium, fluid medium and blood are preferably compartmentalized or separated.

Figure 3:
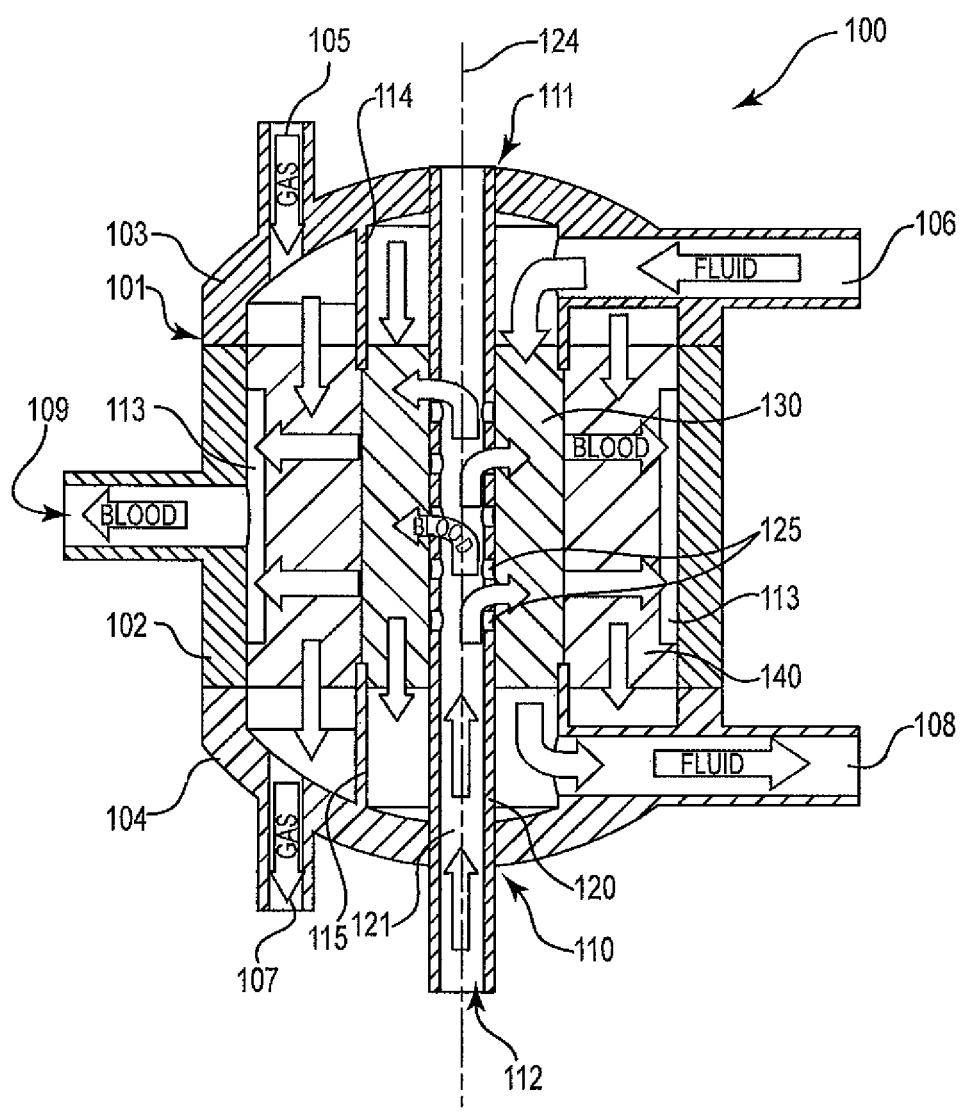
FIG. 3 is a cross-sectional, side view of an embodiment of an apparatus, in accordance with the invention.

FIG. 3 is a cross-sectional view of an embodiment of an apparatus 100 in accordance with the invention. The cross-sectional view in FIG. 3 shows details that may be incorporated into the apparatus of the invention. In addition, FIG. 3 includes arrows showing blood flow and the flow of both fluid and gas media through the apparatus 100.

Apparatus 100 is configured such that a flow of deoxygenated blood from a patient is delivered to a core 120 of the apparatus 100, which comprises an inlet mandrel in the embodiment. Blood enters the inlet mandrel 120, or core, through a blood inlet port 112 and is moved (e.g., pumped by a pump that is not shown) through a lumen 121 of the inlet mandrel 120 and moves radially outward through openings 125 in the inlet mandrel 120 to the heat exchanger 130.

The heat exchanger 130 preferably comprises a bundle or plurality of hollow, heat transfer elements, which may be fibers, tubes, capillaries, compartments, etc. (not shown individually). The heat transfer elements preferably comprise a conductive polymer or a metal. Various shapes of heat transfer elements are contemplated by the invention. One exemplary material for the conduits is polyethylene terephthalate, for example, HEXPETT™ heat exchange capillary, commercially available from Membrana, located in Charlotte, N.C., U.S.A. Other materials are contemplated by the present invention, however. The purpose of the heat transfer elements of the heat exchanger 130 is to transfer heat to or from the fluid medium running there through to or from the blood that flows between the heat transfer elements.

The heat transfer elements of the heat exchanger 130 are located around the core 120, and may be preferably tightly wound or wrapped concentrically about the core 120. Also, the heat transfer elements may be located such that there is minimal or no structural obstruction between the core 120 and the heat exchanger 130. Alternatively to the heat transfer elements actually being wound on the core 120, the heat exchanger may comprise heat transfer elements that are prearranged in a woven, mat or fabric-like arrangement that may be assembled around the core 120, and either in direct contact with the core 120 or such that there is minimal or no structural obstruction to blood flow between the core 120 and the heat exchanger 130.

The heat exchanger 130 may either heat or cool the blood flowing through the apparatus 100. Since hypothermia may be used during cardiac surgery (especially in infant and pediatric surgeries), to reduce oxygen demand, and since rapid re-warming of the blood produces bubble emboli, the heat exchanger 130 is generally used to gradually re-warm blood and prevent emboli formation.

The heat transfer medium used in the heat exchanger 130 may comprise water or other suitable fluids. The heat exchanger 130 may comprise hot and cold tap water that is run through the plurality of heat transfer elements. Preferably, however, a separate heater/cooler unit with temperature-regulating controls is used to heat or cool the fluid medium outside of the apparatus 100, as necessary to regulate the temperature of the blood flowing between the heat transfer elements. As another alternative, a heat transfer means other than a fluid is possible. For example, thermal energy may be supplied to the heat transfer elements rather than a fluid.

FIG. 3 includes arrows (labeled as "FLUID") that show the flow of a fluid heat transfer medium through the heat exchanger 130, with entry at fluid inlet port 106 and exit at fluid outlet port 108. The fluid medium preferably runs through lumens in the plurality of heat transfer elements.

Alternative configurations for heat transfer elements of the heat exchanger 130 are possible. If the heat transfer elements are wound on the core 120, for example, the elements of the heat exchanger 130 may preferably be surrounded by an elastic band or some other thin, flexible, horizontally extending woven interconnect (not shown) in order to hold them together and in place. After winding, ends of the heat transfer elements that are located near the ends of the combination of core 120 and heat exchanger 130 are cut to allow the gas medium to enter lumens in the heat transfer elements.

Figure 4:
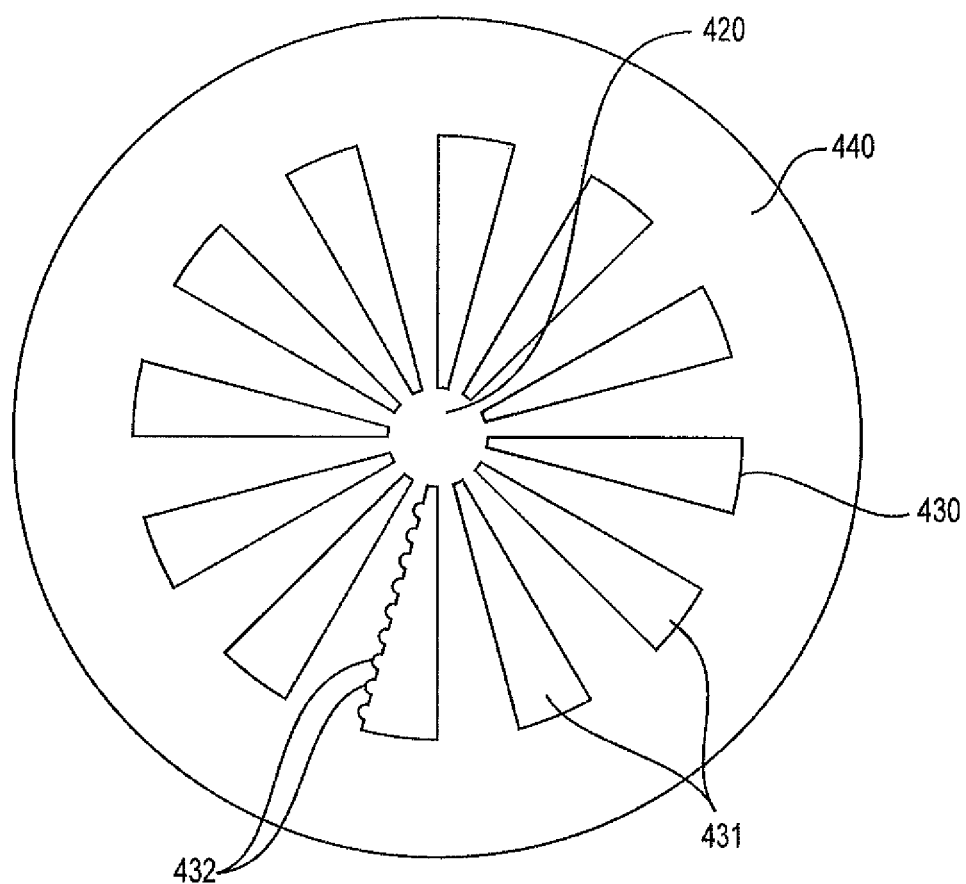
FIG. 4 is a cross-sectional view of a core, an embodiment of a heat exchanger made of a plurality of wedges, and an oxygenator, in accordance with the invention.

Alternatively, the heat exchanger 130 may comprise other materials and other configurations. For example, metal or polymeric tubes may be used. Another alternative is shown in FIG. 4. FIG. 4 shows a cross-sectional view of a core, 420, a heat exchanger 430 and an oxygenator 440, which are components of an embodiment of the apparatus of the invention. In the embodiment, the plurality of heat transfer elements of the heat exchanger 430 comprise a plurality of wedges 431 that are configured and positioned such that blood flowing from the core 420 flows radially outward between the wedges 431. A fluid medium runs through lumens in the wedges 431 in order to transfer heat to or from the blood. The wedges 431 of heat exchanger 430 preferably comprise a metal or a conductive polymer. Preferably, the wedges 431 may be made using an extrusion process.

As another alternative, the wedges may include ribs or ridges 432, or other protrusions, on the surfaces that contact blood. The purpose of the ribs or ridges 432 are to both increase the surface area for heat transfer and to promote mixing to increase convective heat transfer to or from the blood. If an extrusion process is used to make the wedges 431, then the ribs or ridges 432 may be formed during the extrusion process. However, the ribs or ridges 432, or any other protrusions, located on the wedges 431, may alternatively be placed on the surface of the wedges 431 by other means after the wedges 431 are already formed.

Referring again to FIG. 3, other suitable materials and configurations for the heat exchanger 130 that preferably allow the heat exchanger 130 to regulate temperature, have radial flow around substantially all of 360 degrees, and be surrounded by the oxygenator 140, are contemplated by the invention.

After flowing through the heat exchanger 130, blood moves sequentially and radially outward to and through the oxygenator 140 that is arranged around the heat exchanger 130. The oxygenator 140 may concentrically surround the heat exchanger 130. Also, the oxygenator 140 may be wound on the heat exchanger 130. Preferably there is minimal or no structural obstruction to blood flow between the heat exchanger 140 and the oxygenator 140.

The direction of blood flow is preferably maintained as radial, and does not substantially change through the heat exchanger 130 and the oxygenator 140. The direction of blood flow is indicated by the arrows (labeled as "BLOOD").

FIG. 3 also includes arrows that show the flow of an oxygen-containing gas medium through the oxygenator 140 (labeled as "GAS"), with entry at gas inlet port 105 and exit at gas outlet port 107. Preferably, the oxygenator 140 is a membrane oxygenator comprising a plurality of gas exchange elements (e.g., hollow fibers). The blood flowing radially outward from the heat exchanger 130 moves radially between the gas exchange elements that comprise the oxygenator 140. Preferably, a bundle or plurality of hollow fibers are used for gas exchange and are made of semi-permeable membrane including micropores. Preferably, the fibers comprise polypropylene, but other materials are also contemplated by the invention. Any suitable microporous fiber may be used as the gas exchange elements of the oxygenator 140 of the invention.

An oxygen-containing gas medium is provided through the plurality of fibers, or gas exchange elements, comprising the oxygenator 140. An oxygen-rich or -containing gas mixture supplied via the gas inlet 105 travels down through the interior or lumens of the gas exchange elements or fibers. Certain gases are able to permeate the fibers. Carbon dioxide from the blood surrounding the fibers diffuses through the walls of the fibers and into the gas mixture. Similarly, oxygen from the gas mixture inside the fibers diffuses through the micropores into the blood. The gas mixture then has an elevated carbon dioxide content and preferably exits the opposite ends of the fibers that it enters into and moves out of the apparatus 100 through the gas outlet 109. Although oxygen and carbon dioxide are preferably being exchanged, as described above, the invention also contemplates that other gases may be desired to be transferred.

Any suitable gas supply system may be used with the oxygenator 140 of the invention. For example, such a gas supply system may include flow regulators, flow meters, a gas blender, an oxygen analyzer, a gas filter and a moisture trap. Other alternative or additional components in the gas supply system are also contemplated, however.

Gas exchange elements, or fibers, of the oxygenator 140 are arranged around the heat exchanger 130, and preferably in a generally cylindrical shape. The fibers of the oxygenator 140 can be wound directly on the heat exchanger 130. Preferably, in order to form the oxygenator 140, one long microporous fiber may be wound back and forth on the heat exchanger 130. After winding, the fiber is cut at a plurality of locations that are located near the ends of the combination of core 120, heat exchanger 130 and oxygenator 140, which will allow the gas medium to enter the portions of the fiber.

Figure 5A:
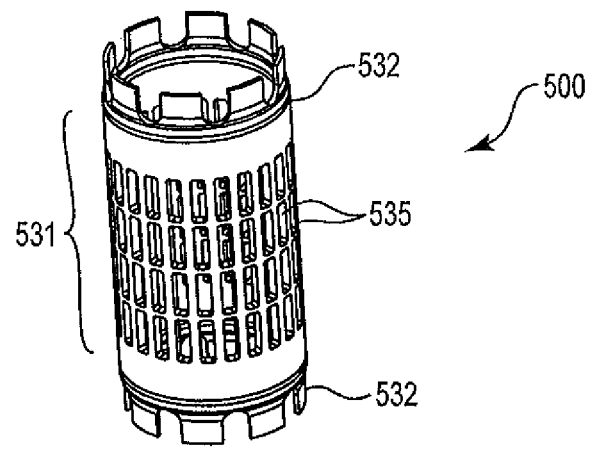
FIG. 5A is a perspective view of a mandrel that may be used with an apparatus, in accordance with the invention.
Figure 5B:
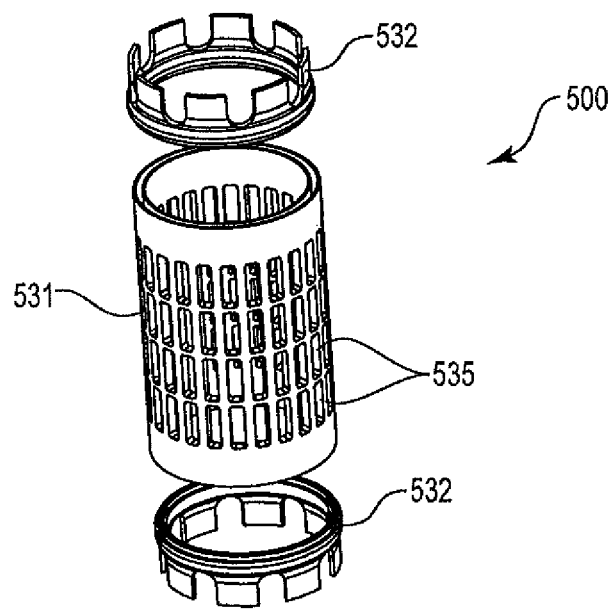
FIG. 5B is an exploded view of the mandrel of FIG. 5A.
Figure 6A:
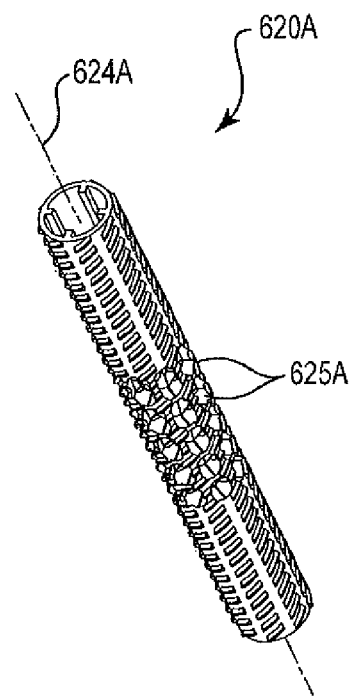
FIG. 6A is a perspective view of an embodiment of an inlet mandrel, in accordance with the invention.
Figure 6B:
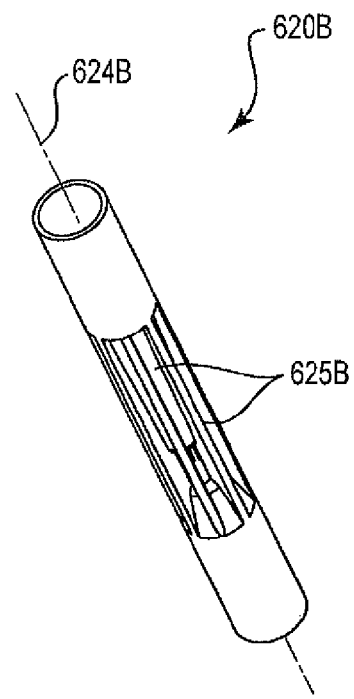
FIG. 6B is a perspective view of an embodiment of an inlet mandrel, in accordance with the invention.
Figure 6C:
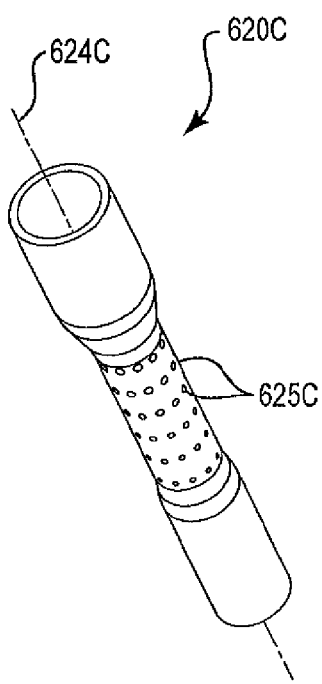
FIG. 6C is a perspective view of an embodiment of an inlet mandrel, in accordance with the invention.
Figure 6D:
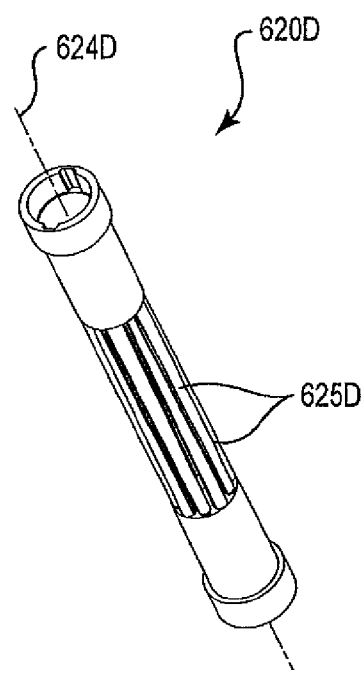
FIG. 6D is a perspective view of an embodiment of an inlet mandrel, in accordance with the invention.

Alternatively, it is contemplated that the oxygenator 140 may be optionally formed by following a method for helically winding continuous, semi-permeable, hollow fiber on some intermediary component rather than directly on the heat exchanger 130. FIGS. 5A and 5B show an exemplary mandrel 500 that may be placed around (e.g., concentrically about) the heat exchanger 130, as in the embodiment of FIG. 3, prior to winding the oxygenator 140 around the heat exchanger 130. The mandrel 500 provides a smooth surface upon which to wind the oxygenator 140. The mandrel 500 also preferably will not interfere with the radial flow of blood through the apparatus 100, and will also preferably have a low prime volume.

The mandrel 500 preferably comprises a center open mesh portion 531 with openings 535 to allow blood to flow there through. The mandrel 500 also preferably comprises two end portions 532. The end portions 532 do not include openings 535. The purpose of the end portions 532 is to separate open ends of the heat transfer elements of the heat exchanger 130 from open ends of the gas exchange elements of the oxygenator 140, when the apparatus 100 is assembled. The ends of the heat transfer elements and gas exchange elements are desired to be separated in order to keep the gas medium and the fluid medium separate in the apparatus 100.

The end portions 532 are preferably attached to the center open mesh portion 531 using tongue and groove joints, as shown. However, it is contemplated that other attachment means may be used. Alternatively, the mandrel 500 may be a unitary piece.

The mandrel 500 may remain in the apparatus 100 as fully-assembled. Alternatively, the mandrel 500 may be removed from the apparatus 100 after the oxygenator 140 has been wound. If the mandrel 500 is desired to be removed, it will be preferably made from a complaint material (e.g., a silicone) to allow for ease in removal. It is possible that the mandrel 500 may be removed manually, by a chemical, or by heat, for example. Other methods of removal of the mandrel 500 are, however, also contemplated by the invention.

Referring to FIG. 3, after blood has traveled radially outward through the apparatus 100, oxygenated blood having a desired temperature is preferably collected along an inner surface of the housing 101 surrounding the oxygenator 140. Preferably, a collection area 113, or space for collection, is provided radially outward from the oxygenator 140 and inside the housing 101. Preferably, the blood in the collection area 113, which surrounds the oxygenator 140, moves along the inner surface of the housing 101 and then flows out of the apparatus 106 through a blood outlet port 109 that is in fluid communication with the collection area 113. Preferably, one outlet port 109 is present, as shown, however, it is also contemplated that there may be more than one outlet port 109.

The configuration and components comprising the core 120 of apparatus 100 begin the radially outward movement or flow of blood through the heat exchanger 130 and oxygenator 140 in apparatus 100. The purpose of the core 120 is to preferably allow blood entering the apparatus 100 to be substantially, continuously, radially distributed into the heat exchanger 130 through substantially all of 360 degrees around the core 120 and along substantially all of the length of the core 120.

As described above, the core 120 of apparatus 100 comprises an inlet mandrel. Blood enters the inlet mandrel 120 through blood inlet port 112 and is moved (e.g., pumped) through lumen 121 and moves radially outward through openings 125 to the heat exchanger 130. Preferably, the inlet mandrel 120 is comprised to allow the blood to move radially outward through substantially all of 360 degrees surrounding the inlet mandrel 120, and also through substantially all of the openings 125 along the length of the inlet mandrel 120. In order to conduct blood flow out of the inlet mandrel 120, the inlet mandrel 120 is preferably shaped using patterns of external features, grooves, protuberances, etc. in order to achieve substantially continuous radial blood flow into the heat exchanger 140. Inlet mandrel 120 may be closed at the end opposite the inlet port 112, but may also preferably include a purge port.

Inlet mandrel 120 is preferably connected to a pump (not shown) or other means for moving blood from a patient into apparatus 100. Pumps that are generally used and known in the art are contemplated to be used with the invention. However, other means for moving the blood that are currently known or that may be developed in the future are also contemplated.

As shown in FIG. 3, the inlet mandrel 120 is preferably generally cylindrical or tubular in shape and includes lumen 121. The inlet mandrel 120 also includes the plurality of openings 125 through which blood is able to flow radially outward from the core 120 with respect to arrangement of the heat exchanger 130 about the inlet mandrel 120. The number of openings 125 provided and the pattern or spacing of the openings 125 in inlet mandrel 120 is configured preferably such that blood may be delivered radially outward from the inlet mandrel 120 substantially through 360 degrees around the heat exchanger 130. Preferably, the blood is able to move radially, which is substantially perpendicular to a longitudinal axis 124 of the inlet mandrel 120.

The inlet mandrel 120 shown in FIG. 3 is one exemplary inlet mandrel that may be used. The inlet mandrel 120 includes a plurality of openings 125 that are substantially circular. Alternative inlet mandrels with alternative openings are also contemplated by the invention. Other exemplary inlet mandrels are shown in FIGS. 6A-6D (as 620A-620D).

The configurations of inlet mandrels 120 and 620A-620D are designed to conduct continuous blood flow radially outward from the inlet mandrels 120, 620A-620D preferably along a substantial length of the inlet mandrel. Preferably, blood from the inlet mandrel moves substantially perpendicular to a longitudinal axis 124, 624A-624D, extending through the inlet mandrel 120, 620A-620D, respectively, and preferably through substantially all of 360 degrees around the longitudinal axis 124, 624A-624D. In order to accommodate such desired blood flow, it is contemplated that many different sizes and shapes of openings 125, 625A-625D, and other external features, grooves, protuberances, etc. may be used.

Another purpose of the configuration of the inlet mandrel is to reduce the amount of prime volume necessary by using the inlet mandrel. Also, the configuration of the inlet mandrel preferably provides a structure onto which heat exchanger material may be wound.

As described earlier, the core of the apparatus of the invention may alternatively include or be replaced by a pump, rather than an inlet mandrel. An embodiment of the invention having a core comprising a pump 727 is an apparatus 700 shown in cross-section in FIG. 7. The apparatus 700 comprises the pump 727, a heat exchanger 730, an oxygenator 740 and a filter 750, which is an optional component of the invention. The pump 727 is preferably located at or near the center of the apparatus 700. The heat exchanger 730 is around the pump 727, and the oxygenator 740 is around the heat exchanger 730.

Alternatively, filter 750 may be arranged around the oxygenator 740. As another alternative, the filter, which includes filter media, may be located such that filter media (not shown separately) may be located between the heat exchanger 730 and the oxygenator 740. As another alternative, a portion of the filter media may be located between gas exchange elements of the oxygenator 740 as they are wound, and another portion of the filter media may be located around the oxygenator 740.

With regard to the heat exchanger 730 and oxygenator 740 in apparatus 700, the description of corresponding components with regard to apparatus 100 in FIG. 3 also applies to the components of apparatus 700. Description of components of apparatus 700 that were not included in apparatus 100 will be described below.

Pump 727 shown is a centrifugal blood pump. Pump 727 generally comprises a rotator 791 that rotates with respect to stator 792 in order to pump blood through apparatus 700. Rotation is caused by magnets 793 located in the rotator 791 interacting with magnets 794 in the housing 701 of apparatus 700.

A particular centrifugal blood pump that may be used in the invention is the Bio-Pump™ Blood Pump, available from Medtronic™, Inc., located in Minneapolis, Minn., U.S.A. Other pumps are contemplated by the invention, however.

Figure 7:
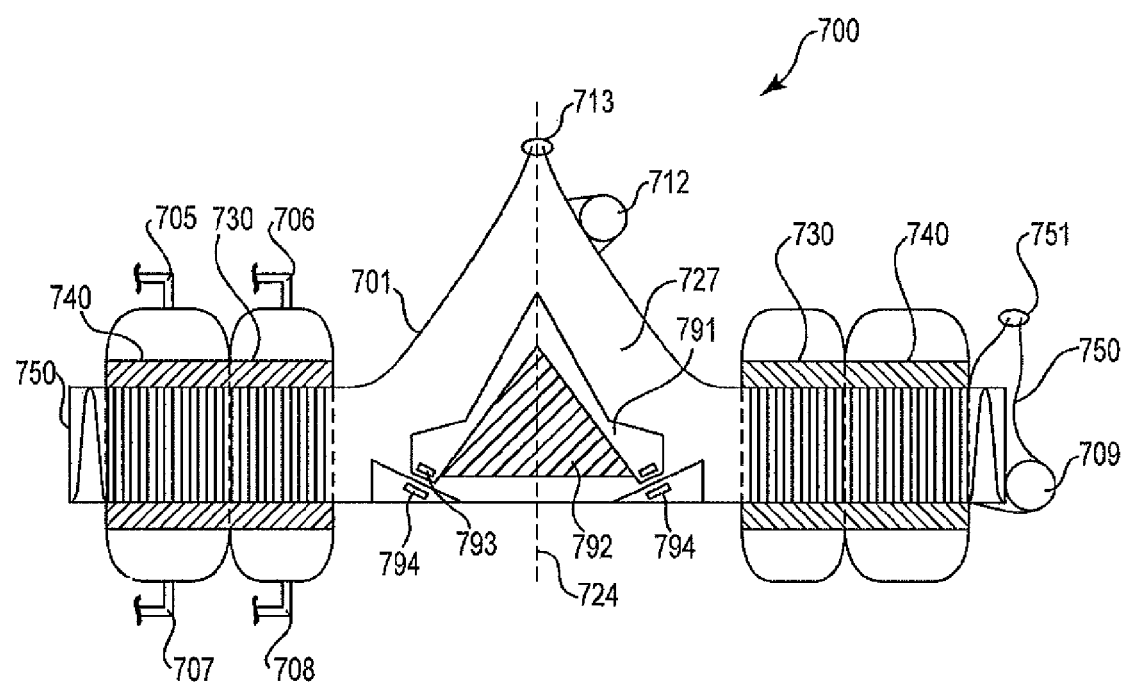
FIG. 7 is a cross-sectional view of an embodiment of an apparatus including a pump, in accordance with the invention.

The particular pump shown in FIG. 7 is exemplary. Many different pumps are contemplated by the invention. For example, some types of pumps that may be used include, but are not limited to, gear pumps, piston pumps, peristaltic pumps, progressive cavity pumps, rotary vane pumps, nutating pumps, flexible liner pumps, diaphragm pumps, centrifugal pumps, flexible impeller pumps, rotary vane pumps, bellows pumps, drum pumps, and rotary lobe pumps. Alternatively, more than one pump may be used in order to achieve desired blood flow through the apparatus.

Pumps are preferably chosen that are able to provide continuous flow. Preferably, the pump is also able to result in radial flow. However, it is contemplated that alternative types of pumps and combinations of pumps may be used with design adjustments being made in the apparatus or system into which the apparatus is incorporated.

The purpose of the pump 727 being located in the core or center of apparatus 700 is to push blood entering through inlet port 712 radially outward through the remainder of apparatus 700. The arrangement of the pump 727, heat exchanger 730 and oxygenator 740 preferably allows blood from a patient to enter the apparatus 700 at blood inlet port 712 and move radially outward through the apparatus 700. The pump 727 preferably propels the blood radially outward through substantially all of 360 degrees surrounding a central axis 724 that extends longitudinally through pump 727. The blood then flows sequentially and radially from the pump 727, into the heat exchanger 730 and then into the oxygenator 740. Optionally, the blood also flows through the filter 750 prior to exiting the apparatus 700 at outlet port 709.

There are two air purge ports that may be preferably included in apparatus 700. One of the ports is purge port 713, which is located in the area of the pump 727. The second port 751 is located in the filter 750 in order to purge any air bubbles that are filtered out of the blood prior to being returned to the patient.

The design and configuration of apparatus 700 is one exemplary such apparatus including a pump in the core. It is contemplated, however, that many other configurations and designs are possible and in accordance with the invention.

Figure 8:
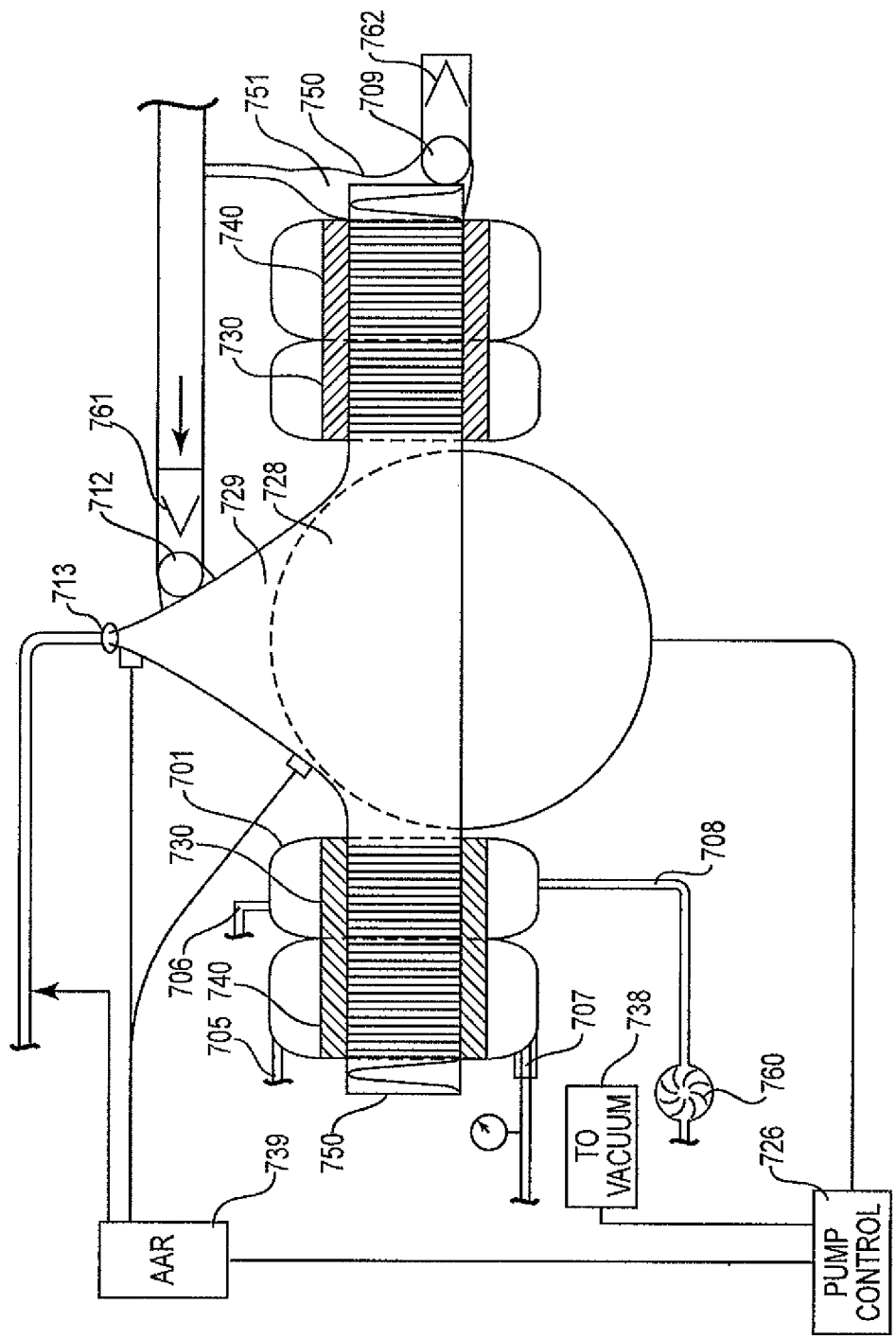
FIG. 8 includes the cross-sectional view of the apparatus of FIG. 7 with an alternative pump and shown with a schematic view of a system into which the apparatus may be incorporated, in accordance with the invention.

FIG. 8 includes the apparatus 700 from FIG. 7 but includes an alternative type of pump, which is a diaphragm pump 729. The figure also includes a schematic representation of a system into which the apparatus 700 may be incorporated.

The description of apparatus 700 above also applies regarding FIG. 8, with the exception of pump 729. The pump 729 shown pumps blood by using a diaphragm 728 that moves up and down, which is different from centrifugal force used in the pump 727 of the embodiment in FIG. 7.

Apparatus 700 in FIG. 8 is shown incorporated into a system. The system shown preferably detects air in the system that is desired to be removed. When air is detected by an integrated active air removal (AAR) device 739, a pump control device 726, that is connected using a circuit line to pump 729, slows the pump 729 until the air is removed. The purpose of the system is to remove any air bubbles that are in the blood before the blood is returned to a patient. Preferably, the active air removal system 739 is incorporated into the top portion of the pump 729, and may alternatively be incorporated into a centrifugal pump (e.g., pump 727 in FIG. 7) with appropriate design adjustments.

The apparatus 700 in FIG. 8 also includes one-way flow valves 761, 762, which are shown as duck-bill valves. Valve 761 is located at the blood inlet port 712, and valve 762 is located at blood outlet port 709. These one-way flow valves 761, 762 are necessary when using a pump, such as pump 729. The purpose of such one-way flow valves is to ensure that the blood flows to the pump 729 of apparatus 700 at blood inlet 712 and out at blood outlet 709.

The system may also preferably include integrated safety features. For example, the system may include a means of assuring that both the gas side pressure and the fluid side pressure in the heat exchanger 730 and oxygenator 740, respectively, are maintained below the blood side pressure. In the system shown, the outlet port 708 on the heat exchanger 730 is under negative pressure. The outlet port 707 of the oxygenator 740 is connected to a vacuum in order to likewise pull the gas medium through the oxygenator 740 under negative pressure. These safety features are included to prevent air bubbles and fluids from being injected into a patient's blood supply as the internal pressures of the device fluctuate due to the action of the diaphragm pump.

Referring again to FIG. 3, an exemplary housing 101 is shown that houses or encloses the core 120, heat exchanger 130 and oxygenator 140 of the invention. The purpose of the design or configuration of the housing 101 is preferably to allow the gas medium, fluid medium and blood to be supplied to different, functional sections of the apparatus 100. The design shown in FIG. 3 prevents undesired mixture of the fluid medium, gas medium and blood. The configuration shown is exemplary, and other configurations are also contemplated by the invention.

The exemplary housing 101 in FIG. 3 is comprised of three main components, which are a cylindrical peripheral wall 102 and first and second end caps 103, 104, respectively. The peripheral wall 102 is preferably open at both ends prior to assembly of the end caps 103, 104, which when assembled provide an enclosure for the components of apparatus 100. The housing 101 also provides inlets and outlets for the blood, the fluid medium used in the heat exchanger 130, and the gas medium used in the oxygenator 140. The peripheral wall 102 of the housing 101 preferably includes a blood outlet 109 for apparatus 100. As shown, the blood outlet 109 preferably comprises a tube or pipe leading away from the apparatus 100, which ultimately allows the blood to be returned to a patient (not shown). Other devices may be necessary in order to return the blood to the patient, but are not shown. An advantage of a single blood outlet 109, as shown, is that the outlet 109 does not substantially interfere with fluid flow dynamics of the radial blood flow in the apparatus 100. Other suitable locations and configurations for a blood inlet or outlet, however, are also contemplated.

The end caps 103, 104 of the housing 101 preferably fit over and are attached to the openings on the ends of the peripheral wall 102 of the housing 101. The end caps 103, 104 also include openings or other inlets and outlets in order for blood, fluid medium and gas medium to move in and out of the interior of the housing 101. As shown, first end cap 103 includes a gas inlet 105 that comprises a pipe or tube, through which a gas mixture containing oxygen is introduced to the oxygenator 140. The first end cap 103 also includes a fluid medium inlet 106 comprising a tube or pipe, through which a fluid medium is introduced to the heat exchanger 130. Second end cap 104 includes a gas outlet 107 and a fluid medium outlet 108, which also both comprise either tubes or pipes, for example. The end caps 103, 104 shown, however, are exemplary and other configurations of such end caps are contemplated by the invention that may complete a housing and permit one or more fluid or gas to flow in and out of the apparatus 100.

Both the first and second end caps 103, 104 also preferably accommodate the core, or inlet mandrel 120. As shown, the inlet mandrel 120 extends through an aperture 110 in the second end cap 104, and into a recession 111 in the first end cap 103. Other configurations of the inlet mandrel 620 in the housing 101 are also contemplated by the invention, and are not limited to those shown or described herein.

Preferably, both end caps 103, 104 are configured in order to provide means for separating fluid and gas flow to the heat exchanger 130 and the oxygenator 140. In particular, ends of the heat transfer elements and gas exchange elements used in the heat exchanger 130 and oxygenator 140, respectively, are separated. A purpose of the end caps 103, 104 is to allow fluid medium, gas and blood to be supplied to different, functional sections of the apparatus and accordingly partition off different fluid or gas flows in order to prevent undesired mixture of the fluid medium, gas and blood.

An exemplary way of separating the ends of the heat transfer elements and gas exchange elements of the heat exchanger 130 and oxygenator 140, respectively, is shown in FIG. 3, and uses walls 114, 115, located in end caps 103, 104, respectively. The circular-shaped walls 114, 115 that extend from the end caps 103, 104 are located such that the walls 114, 115 are lined up where the heat exchanger 130 and oxygenator 140 are adjacent to one another. In particular, the walls 114, 115 preferably separate ends of the heat transfer elements of the heat exchanger 130 from ends of the gas exchange elements of the oxygenator 140, to prevent the fluid medium from mixing with the gas medium. Again, these walls 114, 115 are exemplary, and other configurations are also contemplated by the invention. For example, the oxygenator 140 and heat exchanger 130 may have their end portions staggered in such a way, that the gas medium and fluid medium that are supplied to the two components may be effectively separated.

The first and second end caps 163, 104 and the peripheral wall 102 of housing 101 are preferably connected as shown (FIG. 3). The connection may be provided by attachments means such as screws, adhesives, latches, etc.

Other suitable overall designs for the housing 101 are also contemplated. Alternative housing designs preferably accommodate the radial flow of blood in the apparatus 100 and the arrangement of the oxygenator 140 and the heat exchanger 130 of the apparatus 100, while still allowing the apparatus 100 to fit within a cardiopulmonary bypass circuit.

Figure 9A:
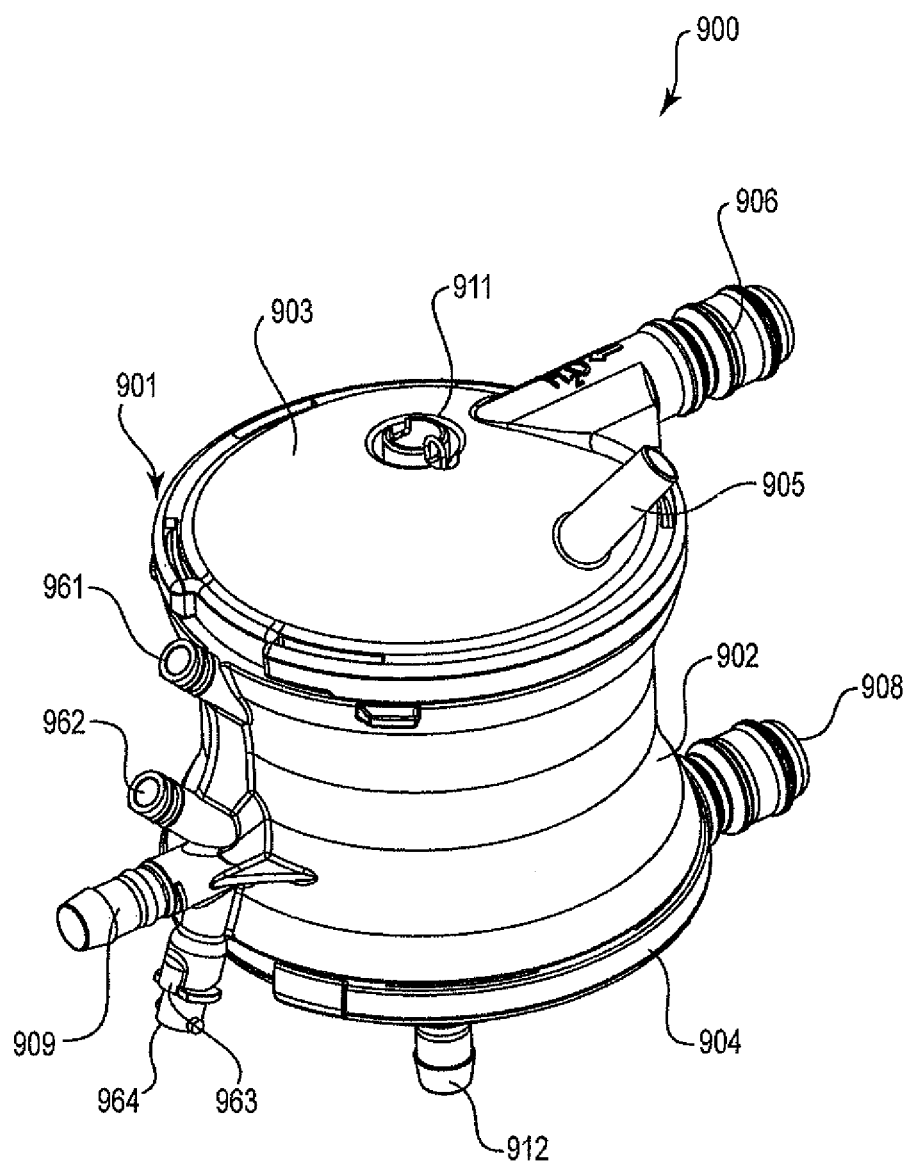
FIG. 9A is a perspective view of an apparatus, in accordance with the invention.
Figure 9B:
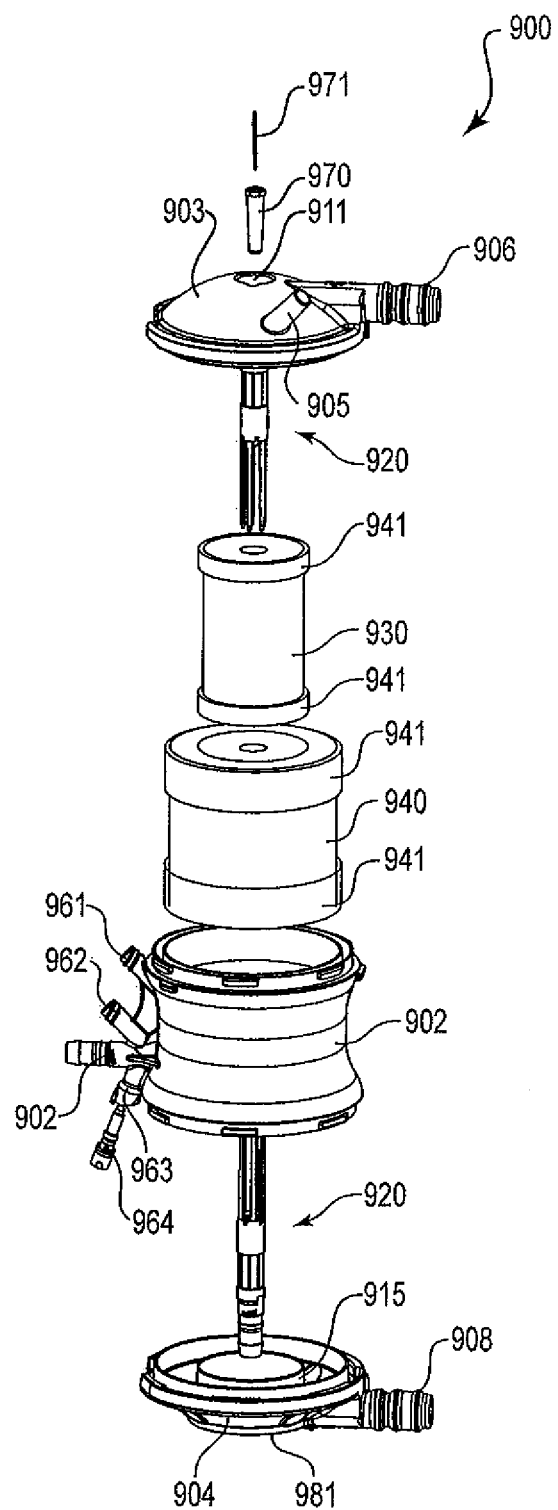
FIG. 9B is an exploded view of the apparatus of FIG. 9A.
Figure 9C:
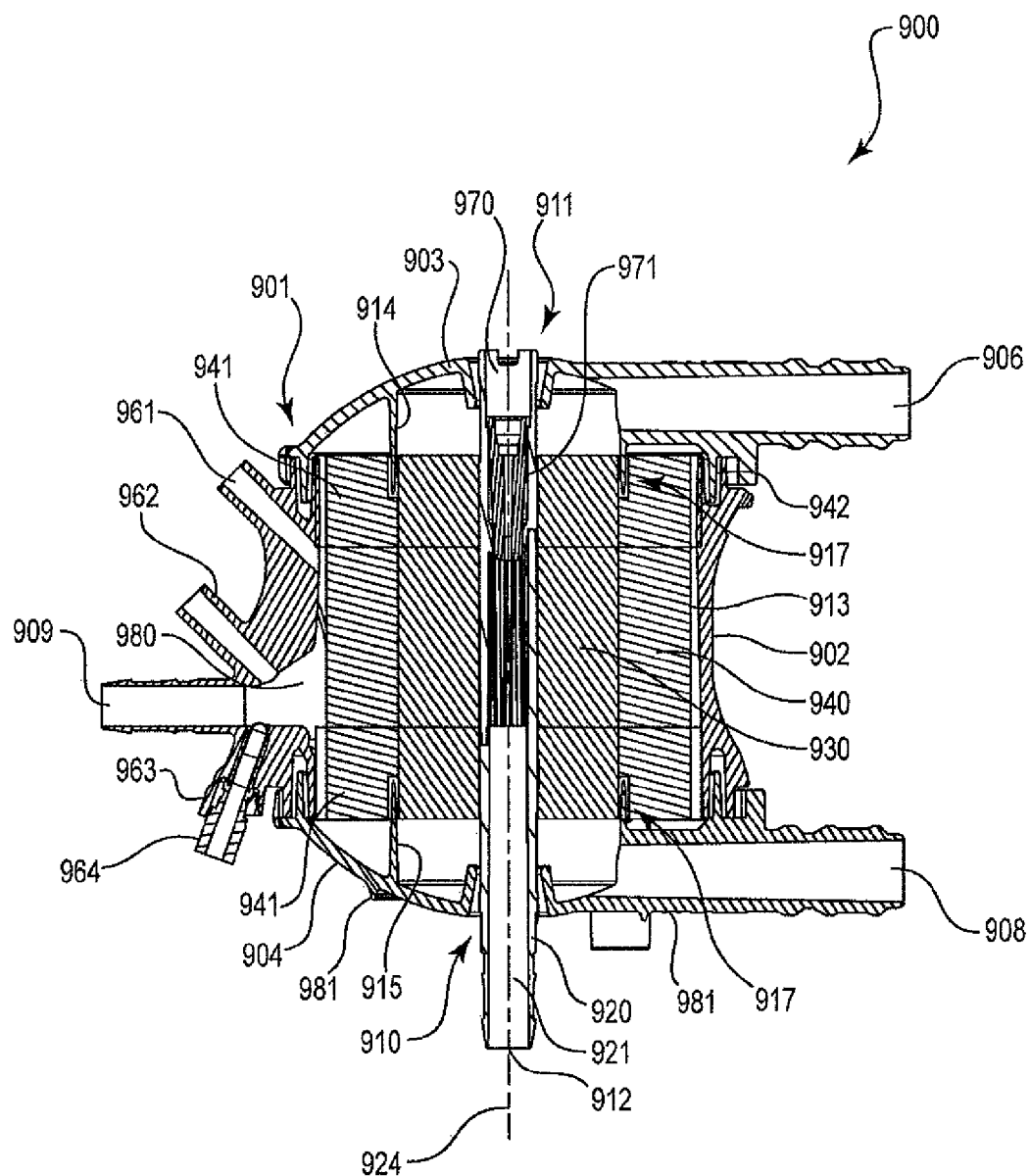
FIG. 9C is a cross-sectional view of the apparatus of FIGS. 9A and 9B.

Another embodiment of an apparatus in accordance with the invention is shown in FIGS. 9A-9C. The apparatus 900 is more detailed than, for example, apparatus 100 in FIG. 3 and apparatus 700 in FIG. 7. With regard to components that have corresponding counterparts in apparatuses 100, 700, the discussion above with regard to apparatuses 100, 700 also applies to the components of apparatus 900. Description of components of apparatus 900 that were not included in apparatuses 100 and 700 or are different will be described below.

Figure 9D:
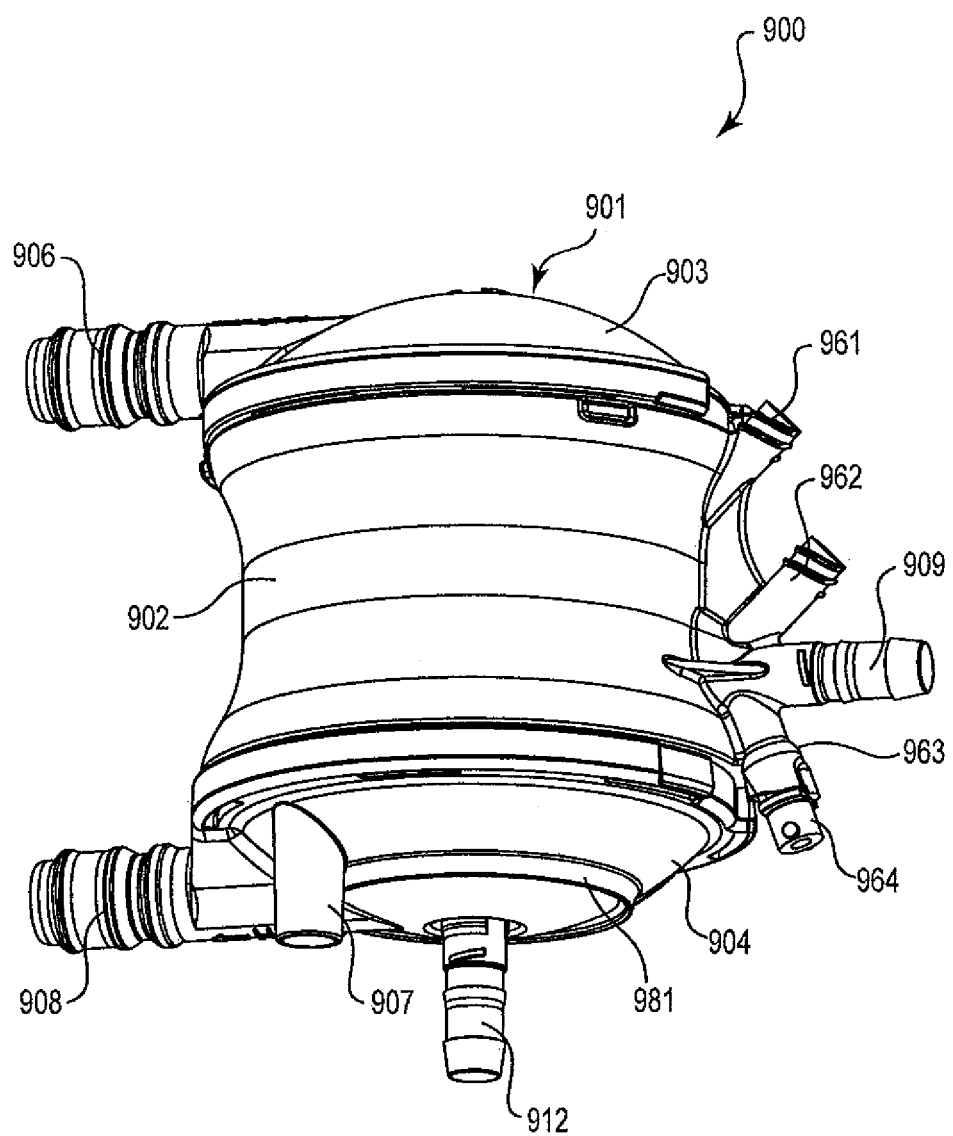
FIG. 9D is an additional perspective view of the apparatus of FIGS. 9A, 9B and 9C.

FIGS. 9A and 9D show perspective views, FIG. 9B shows an exploded view, and FIG. 9C shows a cross-sectional view of another embodiment of an apparatus 900, in accordance with the invention. The embodiment shown includes more details than the previous embodiments.

Apparatus 900 is configured to allow fluid medium, gas medium and blood to be supplied to different, functional sections of the apparatus 900. For example, the gas medium is supplied to an oxygenator 940, and the fluid medium is supplied separately to a heat exchanger 930. Also, the blood delivered to the core 920 is supplied separately. The configuration prevents undesired mixture of the fluid medium, gas medium and blood. The apparatus 900 also is configured such that deoxygenated blood moves radially outward from the core 920 and through the other components, with the fluid medium being supplied to the heat exchanger and the gas medium being supplied to the oxygenator in directions generally transverse to the radial movement of the blood. Again, the configuration shown is exemplary, and other configurations are also contemplated by the invention.

Apparatus 900 includes a core that comprises an inlet mandrel 920, which will be discussed in more detail below. Arranged about the inlet mandrel 120 is a heat exchanger 930. The heat exchanger 930 preferably comprises a bundle or plurality of heat transfer elements (e.g., hollow, heat exchanger conduits) (not shown individually), that are located around the core 920. Preferably, the heat transfer elements are tightly wound or wrapped together adjacent to the core 920, and arranged generally concentrically to enclose or surround the core 920. The heat transfer elements may be wound on the inlet mandrel or may be preformed or arranged in a woven, mat or fabric-like arrangement.

One preferred pre-made heat exchanger mat that is used in apparatus 900 is known as HEX PET™, available from Membrana, located in Charlotte, N.C., U.S.A., which generally comprises two layers of hollow fibers or conduits that are made of polyethylene terephthalate (PET) with the two layers being angled with respect to one another. Preferably, the fibers in one layer are at about a 15 degree angle or bias from normal. Thus, if two layers of the material are layered so that they have opposing biases, the net resulting degree of bias for the fibers between the two layers is 30 degrees. A purpose for the opposing biases is to prevent any nesting of the fibers between the two layers, which could result in increased resistance to blood flow and undesirable and unpredictable shear on the blood flowing there through (i.e., between the fibers). Preferably, the heat exchanger 930 comprises a layer of HEX PET™ that is cut to a certain length from a roll of HEX PET™, and wrapped around itself by using a mandrel, which is then removed from the mandrel and placed concentrically about the inlet mandrel 920 of apparatus 900. Alternatively, the HEX PET™ could be directly wrapped onto the inlet mandrel 920.

As shown, surrounding the heat exchanger 930 is the oxygenator 940. The oxygenator 940 is preferably generally cylindrical in shape and comprises a bundle or plurality of heat exchange elements (e.g., membranous hollow fibers) (not shown individually). The gas exchange elements of the oxygenator 940 are located around, and preferably wound directly on, the heat exchanger 930. Preferably, one or more long microporous fibers are wound back and forth on the heat exchanger 930 many times in a desired pattern to form the oxygenator 940. The preferred method of winding is described in detail below with regard to the method of making the apparatus of the invention.

It is also contemplated that the oxygenator 940 fibers may not be wound directly on the heat exchanger 930, but that a small gap or another material or component may be located between the heat exchanger 930 and the oxygenator 940. An example of such a component is the mandrel 500 shown in FIGS. 5A and 5B, and described above. If a mandrel or separator, like 500, is used, however, it is preferred that the mandrel 500 have a low prime volume.

Preferably, ends of the heat transfer elements comprising the heat exchanger 930 and ends of the gas exchange elements comprising the oxygenator 940 are potted, as described in detail below with regard to the method of the invention. The ends of the heat transfer and gas exchange elements are potted and then a partial depth of the potting is removed from the outer ends in order to allow gas and fluid media communication to the heat transfer and gas exchange elements. FIGS. 9B and 9C show the resultant pottings 941, which are preferably made of polyurethane, although other materials are contemplated.

Apparatus 900 comprises a housing 901 to enclose the other components of the invention. The housing 901, as well as the inlet mandrel 920, are preferably made of a rigid plastic, the purpose of which is for these components to be sturdy yet lightweight. One exemplary type of such a rigid plastic is a polycarbonate-ABS (Acrylonitrile Butadiene Styrene) alloy. Other suitable materials for the housing 901 and inlet mandrel 920 are, however, also contemplated by the invention.

Similar to apparatus 100, the housing 901 of apparatus 900 includes a peripheral wall 902 and first and second end caps 903, 904. The discussion of corresponding components of the housing 901 to housing 101 applies to describe common components. Additional or varying components of the housing 901 of apparatus 900 will be described below.

Apparatus 900 specifically is shown to include tongue and groove joints 942 to connect the peripheral wall 902 and the end caps 903, 904 of the housing 901. The purpose of using tongue and groove joints 942 (FIG. 9C) as connection means is to minimize the risk of leaks. Other suitable connection means or attachment means are also contemplated by the invention, however.

In order to keep the fluid medium in the heat exchanger 930 separate from the gas medium in the oxygenator 940, grooves 917 (FIG. 9C) are preferably formed in the pottings 941. The grooves 917 allow circular walls 914, 915 that are preferably formed on the inner surfaces of the end caps 903, 904 of the housing 901 to fit into the pottings 941. The walls 914, 915 function to separate the ends of the heat transfer elements of the heat exchanger 930 from the ends of the gas exchange elements of the oxygenator 940 in the pottings 941, and keep the gas medium and fluid medium from mixing in the apparatus 900.

Apparatus 901 preferably includes a recirculation line port 961. A recirculation line may be connected to the recirculation line port 961. The port 961 is located such that bubbles that may be produced inside the housing 901 will be collected near the location. The recirculation line may then carry the bubbles back to a venous reservoir, for example, that is preferably a component in a cardiopulmonary bypass circuit of which apparatus 900 may also be a component.

Apparatus 900 also preferably includes a blood sampling port 962. The location of the blood sampling port 962 allows blood samples to be taken from blood before it is returned to a patient. The blood samples may be evaluated for oxygen content, etc.

FIGS. 9A-9D also show apparatus 901 preferably including a temperature probe port 963, which is located such that the temperature of blood being returned to a patient may be monitored. The figures also show a sleeve 964 that fits in the temperature probe port 963 and that preferably includes a temperature sensing or monitoring device, such as a thermister.

Inlet and outlet ports (e.g., ports 906, 908) of apparatus 900 are shown in the figures including features that may not be numbered. For example, ports 906, 908 of the heat exchanger include HANSEN™ fittings (available from Hansen Products, Limited, New Zealand) that are used to hold tubing on the ports, which is a conventional feature of such ports. The blood inlet and outlet ports 912, 909 include barbs as shown in the figures. Other ports may include threads, for example (e.g., port 962) to which an additional component with mating threads may be attached. Again, these are conventional features of such ports, and are not all numbered and specifically described herein.

Apparatus includes a gas outlet port 907 (FIG. 9D). Tubing is preferably connected to the port 907 specifically when an anesthetic is included in the gas medium. If anesthetic is not used, however, gas is generally allowed to flow out of additional holes (not shown in figures) that are open to the air, and located in end cap 904 and in communication with the oxygenator 940.

Housing 901 or apparatus 900 preferably includes a purge port 911 in end cap 903. A purge line, indicated as 970 (FIGS. 9B and 9C), is preferably connected to the purge port 911 in order to allow air to be purged from the apparatus 900.

FIGS. 9B and 9C show a preferred component of apparatus 900, which is a ground wire 971 that is connected to apparatus 900 as shown. The purpose of the ground line 971 is to prevent static electricity from building up between the fluid medium and blood surfaces of the apparatus 900.

Another preferred feature of housing 901 in apparatus 900 is located around the blood outlet 909 and on the inner surface of the peripheral wall 902 of the housing 901. Concave portion 980 (FIG. 9C) allows the blood flowing around the inner surface of the peripheral wall 902, after exiting the oxygenator 940, to more easily flow into the blood outlet 909. The concave shape of concave portion 980 provides some relief as the blood approaches the outlet port 909. The benefit of the shape is that blood flow may more easily converge on the outlet port 909. The radius of the proximal portion of the inside of the outlet port 909 is also preferably optimized to accommodate converging blood flow.

Another optional feature of apparatus 900 may be included on the housing 901. FIGS. 9B, 9C and 9D show a drip ring 981 on end cap 904. The drip ring 981 comprises a protrusion that is preferably circular and surrounds the blood inlet port 912, preferably a distance away from the blood inlet port 912. The drip ring 981 is preferably shaped such that the protrusion extends in the same general direction of the blood inlet 912. This allows any water or other fluid running down the exterior of the housing 901 to contact the drip ring 981 and continue to drip or run down the drip ring 981 and off of the housing 901, while not contacting the blood inlet 912. Other configurations of the drip ring 981 are also contemplated. The drip ring 981 prevents fluid medium from collecting on the end of blood inlet port 912.

The drip ring 981 preferably comprises the same material that is used for the housing 901. However it is contemplated that the drip ring 981 may comprise any suitable material. The drip ring 981 may be formed on the housing 901 at the time of manufacture of the housing 901. For example, the housing 901, including the drip ring 981, may be injection molded. Alternatively, the drip ring 981 could be added to the housing 901 after formation of the remainder of the housing 901.

Although not shown in the figures, an optional addition to portions of the peripheral wall 902 of housing 901 may be included. Ribs may be formed in the inner surface of the peripheral wall 902 near the two open ends. After potting the ends of the heat transfer elements of the heat exchanger 930 and the gas exchange elements of the oxygenator 940, the resultant portion is enclosed in the housing 901, with the inlet mandrel 920 extending there through. The pottings 941 are generally and preferably lined up with the inner surface of the peripheral wall portion 902 in the area of ribs that are preferably formed in the inner surface. The potting composition used, such as polyurethane, may shrink with time. The pottings 941 may be made to extend into the optional ribs, which decreases the chance of the pottings 941 delaminating from the housing 901 due to shrinkage. Therefore, the ribs are optional, but are preferred in order to keep the heat exchanger 930 and oxygenator 940 in place in the apparatus 900.

In order to begin radial movement of blood through apparatus 900, blood enters the apparatus 900 through the inlet mandrel 920. The inlet mandrel 920 is configured so as to effectively distribute blood along substantially all of the length of the inlet mandrel 920, in a direction that is generally perpendicular to a longitudinal axis 924 extending through the inlet mandrel 920 (in FIG. 9C), around substantially 360 degrees with respect to the axis 924, and into adjacent heat exchanger 930. Preferably, the inlet mandrel comprises a first element and a second element that interfit to define openings. The elements and the openings together enhance flow of blood radially outward from the inlet mandrel.

The inlet mandrel 920 is preferably generally cylindrical or tubular in shape and includes a delivery passageway or lumen 921. The inlet mandrel 920 includes openings or slots 925 through which blood is able to flow radially outward there from. The number, pattern and shape of openings or slots 925 is provided in order to provide desired radial blood flow through apparatus 900 with minimal trauma to the blood. It is contemplated that alternative inlet mandrels to inlet mandrel 920 may be included in apparatus 900.

Figure 10A:
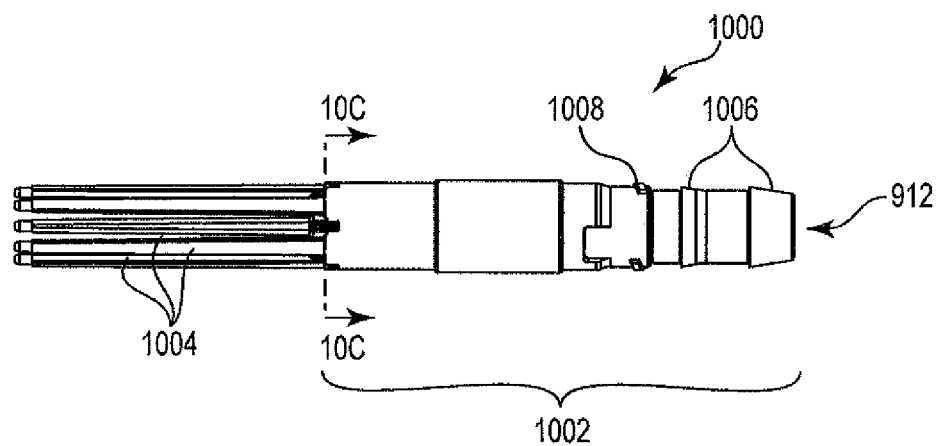
FIG. 10A is a side view of an inlet side element of an embodiment of an inlet mandrel, in accordance with the invention.
Figure 10B:
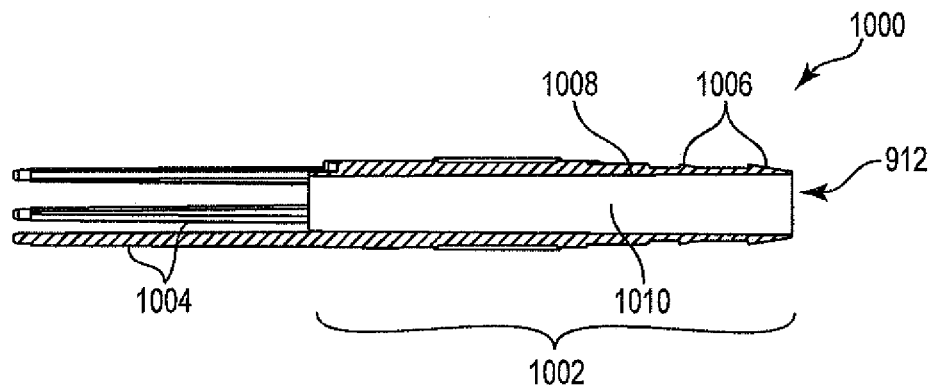
FIG. 10B is a cross-sectional view of the inlet side element in FIG. 10A.
Figure 10C:
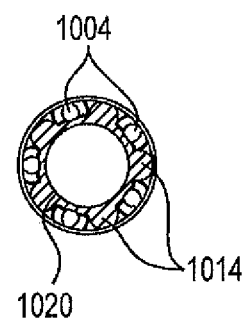
FIG. 10C is cross-sectional view taken at cut 10C in FIG. 10A.
Figure 11A:
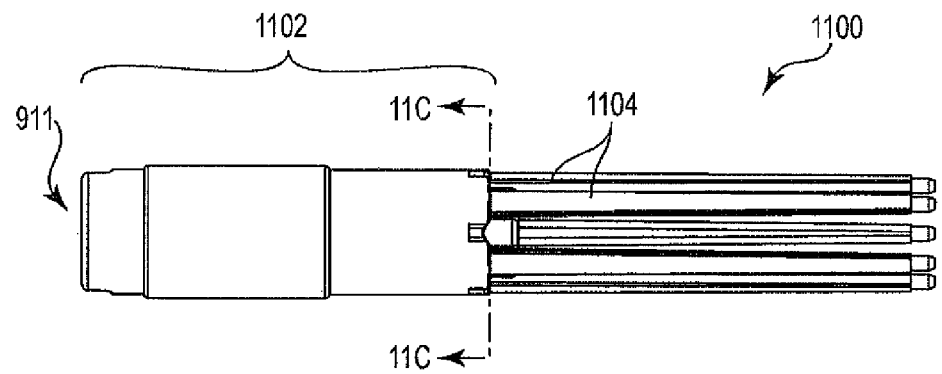
FIG. 11A is a side view of a purge port side element of an embodiment of an inlet mandrel, in accordance with the invention.
Figure 11B:
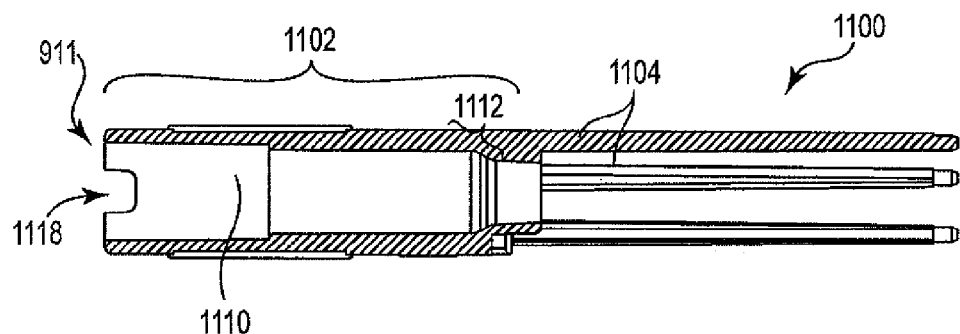
FIG. 11B is a cross-sectional view of the purge port side element in FIG. 11A.
Figure 11C:
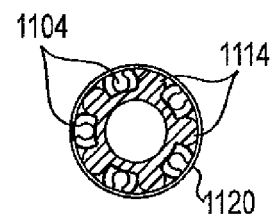
FIG. 11C is cross-sectional view taken at cut 11C in FIG. 11A.
Figure 12A:
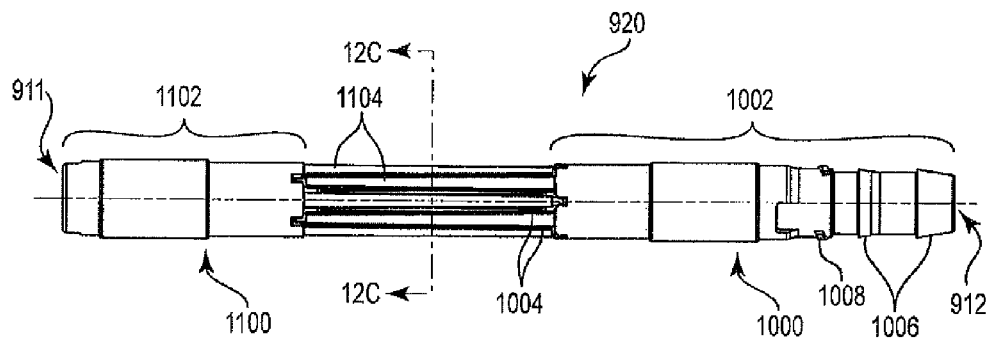
FIG. 12A is a side view of an assembled inlet mandrel including the inlet side element of FIGS. 10A-10C and the purge port side element of FIGS. 11A-11C, in accordance with the invention.
Figure 12B:
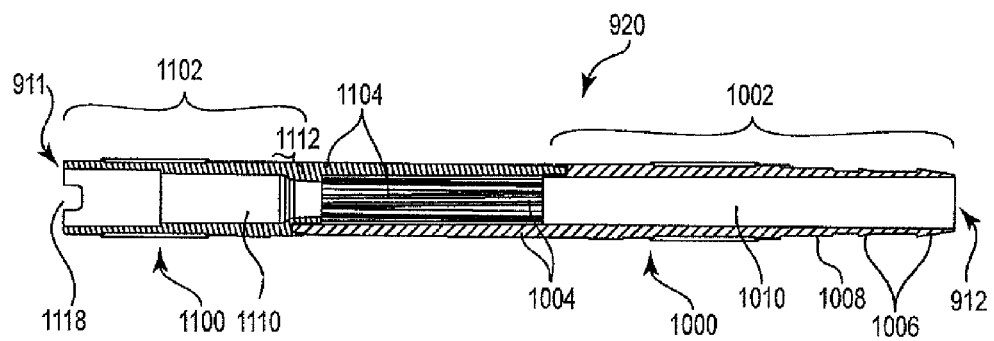
FIG. 12B is a cross-sectional view of the inlet mandrel in FIG. 12A.
Figure 12C:
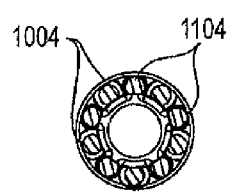
FIG. 12C is cross-sectional view taken at cut 12C in FIG. 12A.

FIGS. 11A-12C provide views of inlet mandrel 920 and the components that comprise the inlet mandrel 920. Inlet mandrel 920 is comprised of two elements, parts or portions that fit or mate together and are preferably secured together, which are a blood inlet side component or element 1000 (shown in FIGS. 10A-10C) and a purge port side component or element 1100 (shown in FIGS. 11A-11C). FIGS. 12A-12C show the inlet side element 1000 and purge port side element 1200 assembled, which forms inlet mandrel 920.

The inlet side element 1000 is generally comprised of a body segment 1002 that is attached to a plurality of tines 1004. The body segment 1002 includes the blood inlet port 912 for the apparatus 900. The body segment 1002 preferably includes barbs 1006 that are provided in order to hold tubing (not shown) to the inlet mandrel 920, through which blood is supplied from a patient to the inlet mandrel 920. The body segment 1002 also preferably includes a luer thread 1008 that is provided so that other components may be assembled to the inlet mandrel 920. For example, the luer thread 1008 may be used to attach adapters (not shown) to the inlet side element 1000 that can accommodate different sizes of tubing that may be attached to the inlet mandrel 920. The body segment 1002 may also include other details that may be necessary in order to manufacture the inlet side element 1000. The body segment 1002 also includes recesses 1014 into which tines on the purge port element 1100 are fit. The recesses 1014 (shown in FIG. 10C) are shaped in order to accommodate tines on purge port side element 1100.

Inlet side element 1000 comprises the plurality of tines 1004 that are attached to the body segment 1002 preferably in a circular pattern, as shown in FIG. 10C. The tines 1004 are preferably evenly spaced around the circular end of the body segment 1002, and preferably alternate with the recesses 1014. A preferred number of tines 1004 and recesses 1014 each is five, but other numbers of tines and recesses are also contemplated. The number of tines 1002, as well as the shape and configuration of the tines 1004, is provided in order to allow blood to flow radially outward from the inlet mandrel 920 continuously and evenly while reducing the amount of trauma to the blood.

Preferably, the tines 1004 have a kidney-bean-shape that is wider toward the lumen 1010 and narrower away from the lumen 1010. This preferred shape contributes to a desired radial blood flow between the tines 1004, as well as tines 1104 (FIGS. 11A-11C) of the purge port side element 1100. The cross-section of the tines 1004, 1104 preferably tapers away from the lumens 1010 and 1110 in both elements 1000, 1100 so that there is less surface area contacted by heat exchanger material that is wound around the inlet mandrel 920. This allows blood to move around the tines 1004, 1104 and into the heat exchanger 930 more easily.

The tines 1004, 1104 are also preferably tapered along their length and toward their ends in order to fit in the recesses 1014 (and recesses 1114 in element 1100) on the opposing element (1000 or 1100) of inlet mandrel 920. The cross-sectional views in FIGS. 10C and 11C show the tapering by including taper lines 1020, 1120.

Purge port side element 1100 (FIGS. 11A-11C), being similar to inlet side element 1000, also includes a body segment 1102. Body segment 1102 also includes recesses 1114 into which tines 1004 on the opposing element, inlet side element 1000, are secured. Body segment 1102, however, includes features that are different from those of inlet side element 1000, and for example, features that allow air to be purged from the inlet mandrel 920 as may be desired at purge port 911. A notch 1118 may be included in body segment 1102 in order to accommodate a plug (970 in FIG. 9C), for example.

Purge port side element 1100 also preferably includes five tines 1104 that are attached to body segment 1102. However, alternative numbers, shapes and configurations to those tines shown are also contemplated. The tines 1104 of purge port side element 1100 are fit into recesses 1014 in inlet side element 1000, and the tines 1004 of inlet side element 1000 are fit into recesses 1114 in purge port side element 1100, and may be preferably secured using an adhesive, for example. FIGS. 12A-12C illustrate the inlet side element 1000 and the purge port side element 1100 as assembled to form inlet mandrel 920.

Within the lumens 1010, 1110 of the body segments 1002, 1102 of elements 1000, 1100, respectively, generally any transitions (e.g., transition 1112 in FIG. 12B) are stepped transitions that are preferably stepped-down. Therefore, in the direction of blood flow through the lumens 1010, 1110, the diameter of the particular lumen 1010 or 1100 may increase in diameter at the transitions. Blood flow through elements 1000, 1100 is from the blood inlet port 912 in element 1000 towards the purge port 911 in element 1100 (right to left in FIGS. 12A and 12B). The purpose of stepping-down the transitions is to prevent trauma to blood cells flowing by the transitions.

In particular, apparatus 900 is designed for pediatric use. However, it is contemplated by the invention that changes may be made with regard to apparatus 900 as described herein in order to use the apparatus 900, for example, with adult patients. For instance, the apparatus 900 may be available in different sizes to accommodate different sizes of patients, for example, adult patients. In addition, other components may be necessary in order to accommodate adult patients.

Apparatus 900, in accordance with the invention, may be used or incorporated into any appropriate system or device in which blood is desired to be oxygenated and temperature-controlled. One particular system is an electromechanical extracorporeal circulatory support system known as a cardiopulmonary bypass (CPB) system, commercially sold by Medtronic, Inc. (Minneapolis, Minn., U.S.A.), which is called the Performer-CPB System. Other systems are contemplated by the invention, however.

The following description addresses a method of making an apparatus such as the embodiments of the apparatus of the invention, as described above. In particular, the description of the method will describe making apparatus 900. However, it is contemplated that the method may be applied to other such apparatuses as well, which may require additional steps, fewer steps, or alternative steps.

In order to make apparatus 900, first, an inlet mandrel 920 is received or provided. Alternatively, the core may include a pump, as in apparatus 700. The inlet mandrel 920 is assembled, as described above. The other components of apparatus 900 will be arranged around the inlet mandrel 920.

With some inlet mandrels, it may be necessary to extend a supportive mandrel through the lumen of the inlet mandrel for assembly purposes. The inlet mandrel may comprise more than one piece or element, which may be assembled over the supportive mandrel. In order to hold the pieces or elements of the inlet mandrel to the supportive mandrel and together, shrink wrap or heat shrink tubing may be applied to the ends of the inlet mandrel 920.

Next, the heat exchanger 930 is concentrically arranged about the inlet mandrel 920. Heat exchanger material may be wound on the inlet mandrel 920. Alternatively, the heat exchanger 930 may be wound and formed into a mat-like material separately, and then wrapped around the inlet mandrel 920 subsequently. Preferably, a pre-made heat exchanger mat that is used in apparatus 900 is known as HEX PETT™, as discussed above. Tape is preferably used to start and end the wind of the HEX PET™ on the inlet mandrel 920. The heat exchanger 930 will be arranged or wound such that ends of the plurality of heat transfer elements that form the heat exchanger 930 may be in fluid communication with the fluid medium. The fluid medium will be provided to one (of two) end of the heat transfer elements and removed from the other end of the heat transfer elements.

Next, the oxygenator 940 is arranged concentrically about the heat exchanger 930. A fiber or plurality of gas exchange elements comprising the oxygenator 940 may be located around or wound directly on the heat exchanger 930. Alternatively, a mandrel, such as mandrel 500 in FIGS. 5A and 5B, may be placed on the heat exchanger 930 before the oxygenator 940 is wound onto the heat exchanger 930. Such a mandrel may remain in place or may be subsequently removed before the apparatus 900 is used.

The oxygenator 940 may be formed by using a known method for helically winding continuous semi-permeable hollow fiber. The method is described in U.S. Pat. No. 5,346,612, which is incorporated herein by reference in its entirety. The known method may be used to instead wind hollow fiber, for example, on the heat exchanger 940 to produce the oxygenator 940 for use in apparatus 900.

Figure 13:
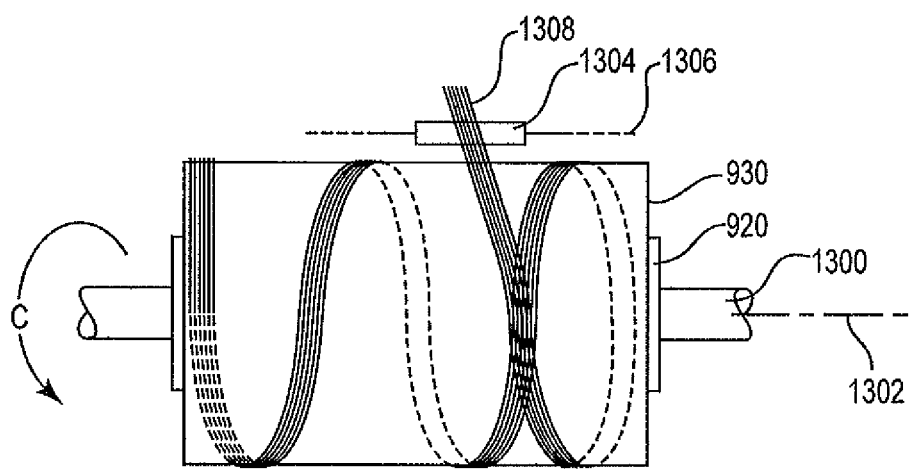
FIG. 13 is a schematic view showing oxygenator fibers being wound on a heat exchanger in the early stage of the winding process, in accordance with the invention.

Generally, a winding apparatus, as shown in FIG. 13, is provided, which has a rotatable mounting member 1300 having a longitudinal axis 1302 and a fiber guide 1304 adjacent said mounting member 1300. The fiber guide 1304 is adapted for reciprocal movement along a line 1306 parallel to the longitudinal axis 1302 of said mounting member 1300 as the mounting member 1300 rotates. The heat exchanger 930 and inlet mandrel 920 combination is mounted for rotation on the rotatable mounting member 1300. At least one continuous length of semi-permeable hollow fiber 1308 (although more than one is shown) is provided where the hollow fiber is positioned by said fiber guide 1304 and secured to said heat exchanger 930. The mounting member 1300 is rotated and the fiber guide 1304 is moved reciprocally with respect to the longitudinal axis 1302 of the mounting member 1300. Fiber or fibers 1308 is or are wound onto said heat exchanger 930 to form the oxygenator 940 which extends radially outward relative to the axis of the mounting member 1300 and which preferably has packing fractions which increase radially outwardly throughout a major portion of said oxygenator 940, thereby preferably providing a packing fraction gradient.

The foregoing method may involve two or more fibers 1308 positioned by the fiber guide 1304. The two or more fibers 1308 are wound onto the heat exchanger 930, or an intermediary component, to form a wind angle relative to a plane parallel to the axis of the heat exchanger 930, tangential to the point at which the fiber is wound onto said heat exchanger 930 and containing said fiber 1308.

Figure 14:
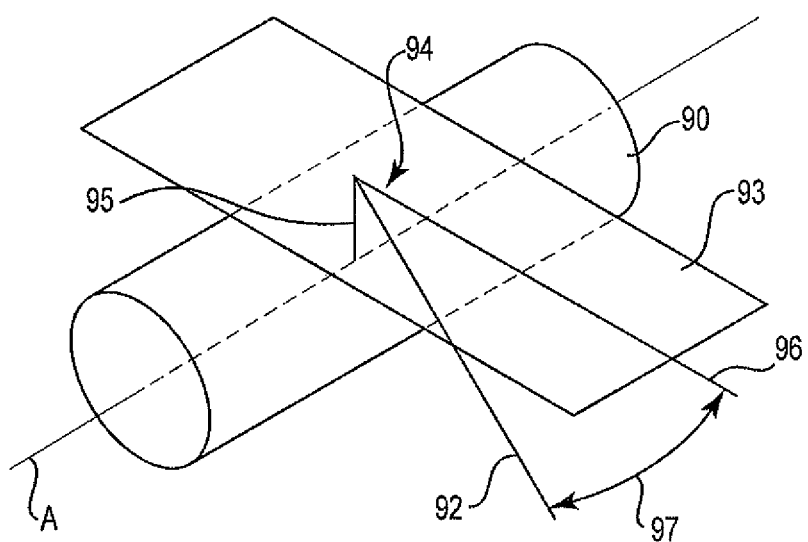
FIG. 14 is a schematic representation of a winding apparatus for the method of winding oxygenator fibers, in accordance with the invention.

FIG. 14 illustrates the wind angle for a single fiber, but would apply as well for each of two or more fibers. Fiber 92 is contained in plane 93. Plane 93 is parallel to axis A of core 90. Plane 93 is tangential to point 94 at which fiber 92 is wound onto core 90. Line 95 is perpendicular to axis A and passes through point 94 and axis A. Line 96 is a projection into plane 93 of the normal line 95. Wind angle 97 is measured in plane 93 between projection line 96 and fiber 92. Alternatively, line 92 in tangential plane 93 is a projection into plane 93 from a fiber (not shown) which lies outside of plane 93.

The wind angle may be increased by increasing the distance through which the fiber guide moves during one rotation of the mounting thereby providing said increasing packing fraction. The wind angle may be decreased, increased or otherwise varied outside of the major portion of the bundle. The wind angle will be considered to have increased in the major portion of the bundle if on average it increases even though it may vary including decreasing.

The winding method may further involve tensioner means for regulating the tension of said fiber as it is wound. The tension of said fiber may be increased stepwise and continuously throughout a major portion of such winding thereby providing said increasing packing fraction. The fiber guide may be adapted to regulate the spacing between two or more fibers being simultaneously wound and the spacing may be decreased throughout a major portion of such winding thereby providing said increasing packing fraction.

The above-outlined procedure for spirally winding semipermeable hollow fiber on a supporting core, such as on heat exchanger 930, for use in the blood oxygenator in accordance with the present invention is set forth in U.S. Pat. No. 4,975,247 ("'247 patent") at column 9, line 36 through column 11, line 63, including FIGS. 12 through 16A, all of which are incorporated herein by reference thereto for showing the following winding procedure. FIG. 16 of the '247 patent shows an alternative method for making a fiber bundle wherein a two-ply fiber mat 75 is rolled onto a core.

Guide 1304 travels from the first end (left hand side of FIG. 13) of the heat exchanger 930 to the second end (right hand side of FIG. 13) where it decelerates. After decelerating, the guide 1304 reverses direction and travels back to its starting position. After decelerating again and reversing direction, the guide begins its travel cycle anew. This reciprocal travel for guide 1304 and the concurrent rotation of mounting member 1300 on which the heat exchanger 930 has been mounted is continued, subject to the following described alteration, until an oxygenator 940 of desired diameter has been wound onto the heat exchanger 930.

As described more fully in columns 10-11 of the '247 patent, in the left-to-right travel of guide, a fiber ribbon was wound spirally around an extended support core (heat exchanger 930 in this invention) and the individual fibers in the ribbon were laid down in contact with the outer surfaces of support core ribs. In the known winding procedure, the core (heat exchanger 930 in this invention) is covered, except for the spacing between adjacent fibers and the distance between the sixth fiber of one ribbon and the first fiber of the next adjacent ribbon, when the fiber guide has traveled a sufficient number of traverses.

An exemplary pattern of winding the fibers of the oxygenator 140 is found on the Affinity™ Oxygenator (commercially available from Medtronic, Inc., Minneapolis, Minn., U.S.A.). However, alternatively, other methods and patterns of winding the oxygenator 140 fibers are also contemplated by the invention.

An optional additional component that may be incorporated into apparatus 900 is a filter. Although not shown, it is contemplated that such a filter may be located in various locations within the apparatus 900. For example, the filter may be located around the oxygenator 940. Another possible location for the filter is between the heat exchanger 930 and the oxygenator 940. Yet another possibility is for fiber media of the filter to be located in between wound fibers or gas exchange elements of the oxygenator. For example, during winding of gas exchange elements or fibers comprising the oxygenator 940, the winding is interrupted and filter media is placed around the fibers or gas exchange elements, and then winding is continued to complete the oxygenator 940. An advantage of locating filter media within the oxygenator 940 is that blood running between the gas exchange elements of the oxygenator is oxygenated, then filtered, and then oxygenated again after filtering thereby bringing the level of oxygen in the blood up to a desired level after filtration. Other configurations or design of the apparatus 900 including a filter (not shown) are contemplated by the invention and are not limited to those described herein.

In making apparatus 900, once the oxygenator 940 is wound on the heat exchanger 930 (with or without any other components or space in between), ends of the heat transfer elements of the heat exchanger 930 and the gas exchange elements of the oxygenator 940 are preferably embedded in a potting composition in order to hold them together and in place in apparatus 900. The preferred potting material is polyurethane introduced by centrifuging and reacted in situ. Other appropriate potting materials or methods of potting the heat exchanger 930 and oxygenator 940 portions of the apparatus 900 are also contemplated by the invention.

Preferably, the potting composition is applied to both ends of the sets or pluralities of gas exchange elements and heat transfer elements that make up the oxygenator 940 and heat exchanger 930, which results in two regions of potted material. The potting material, however, covers the ends of the elements as well when applied in such a manner. Therefore, it is usually necessary to open the end of the heat transfer elements and gas exchange elements in order to allow communication with the gas and fluid media introduced to apparatus 900. Thus, once cured, a partial depth of the outer ends of the pottings 941 are preferably sliced or cut (i.e., "guillotined") in order to expose or open lumens of the heat transfer elements and gas exchange elements to allow gas and fluid media to be supplied to the lumens. Preferably, the potted ends are partially cut through in order to open the lumens of the heat transfer elements and gas exchange elements. The potted and cut ends of the heat transfer elements and gas exchange elements are then placed in the housing 901 such that the lumens of the heat transfer elements are in communication with the heat transfer medium and the lumens of the gas exchange elements are in communication with the oxygen-containing gas medium. As shown in the figures, the pottings are preferably located in the first end cap 903 and the second end cap 904, and in communication with gas medium and fluid medium supplied to apparatus 900. The portions of the heat exchanger 930 and oxygenator 940 that are potted in such a way are called "pottings," and are indicated as 941.

The fluid medium inlet 908 provides water, or another fluid medium, to the heat exchanger 930, in particular to one end of the plurality of heat transfer elements (not shown). The fluid medium is preferably heated or cooled outside of the apparatus 900, as necessary to regulate the temperature of blood flowing through the heat exchanger 930. The use of a countercurrent flow heat exchanger 940 provides optimum heat exchange efficiency. The temperature of the blood can be monitored by a circuit (not shown) that includes a thermister or other temperature sensing device (not shown) mounted inside apparatus 700. After flowing through the heat exchanger 930, the fluid medium flows out of the heat exchanger 930 and the apparatus 900 through the fluid medium outlet 908.

After slicing the pottings 941 and subsequent assembly of the apparatus 900, the lumens of the plurality of gas exchange elements of the oxygenator 940 are also able to be in communication with the gas inlet 905 and gas outlet 907. The oxygenator 940 is preferably supplied with a gas mixture rich in oxygen from a pressurized source (not shown) which is conveyed to the oxygenator 940 through gas inlet manifold 905.

As also described above, it may be preferable to separate the ends of the heat exchange elements from the ends of the gas exchange elements within the pottings 941. In particular, one method for separating the ends is to create a channel in between the heat transfer elements and the gas exchange elements. The channel may be created using removable hubs, bands or rings.

Figure 15:
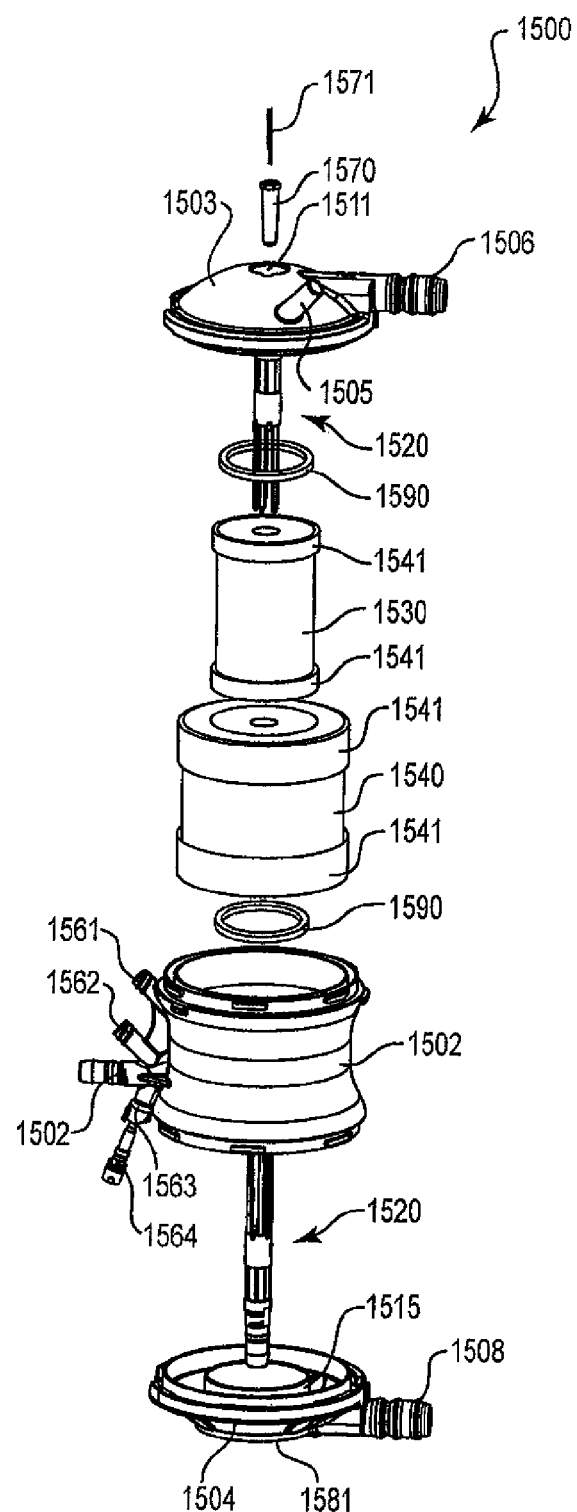
FIG. 15 is an exploded view of an embodiment of an apparatus, in accordance with the invention.

FIG. 15 is an exploded view of another embodiment of an apparatus 1500 of the invention. In particular, apparatus 1500 includes two hubs 1590 in order to form a channel in each of the pottings 1541. The remainder of the components of apparatus 1500 are similar to those described in earlier embodiments.

The hubs 1590, or circumferential elements, are removable and may be comprised of any material that is able to form a circular structure. Preferably, the material does not adhere to urethane. The hubs 1590 may be formed by being molded or extruded, for example.

Two removable hubs 1590 are placed between the heat exchanger 1530 and oxygenator 1540, and in particular near the two ends of the heat exchanger 1530 and oxygenator 1540 combination (one hub on each end), during assembly. The hubs 1590 are placed to surround the heat exchanger 1530 near the ends and are placed on the heat exchanger 1530 ends prior to winding of the oxygenator 1540. The hubs 1590 are left in place until after the ends of the heat transfer elements and the gas exchange elements are potted and sliced to form pottings 1541. The hubs 1590 are then removed, for example, either manually, by heat, by chemistry, etc. The space or groove left behind (not visible in FIG. 15, but like 917 in apparatus 900) in the pottings 1541 is then preferably at least partially filled by a portion of the housing of the apparatus (e.g., walls 1514, 1515 on end caps 1503, 1504) in order to separate the ends of the heat transfer element of the heat exchanger 1530 from the ends of the gas exchange elements of the oxygenator 1540 in order to eliminate possible pathways for leaks.

Referring back to apparatus 900, next, the pottings 941 are enclosed in housing 901. With the housing 901 shown in FIG. 9A, for example, the end caps 903 and 904 are bonded or attached to the peripheral housing portion 902, in order to enclose the heat exchanger and oxygenator. Additional components of the housing 901 are also preferably adhered together to form the apparatus 900. Adhesive or other means for bonding the components together are contemplated.

While the invention has been described with preferred embodiments, it is to be understood that variations and modifications may be resorted to as will be apparent to those skilled in the art. Such variations and modifications are to be considered within the purview of the scope of the invention.

All patents, patent applications and publications mentioned herein are incorporated by reference in their entirety.

The invention claimed is:

1. An apparatus for oxygenating and controlling the temperature of blood in an extracorporeal circuit, the apparatus having a blood inlet and a blood outlet that is located radially outward from the blood inlet in order to define a flowpath through the apparatus, the apparatus comprising:
   a core that is substantially centrally located in the apparatus and to which blood from a patient can be supplied through the blood inlet, the blood inlet being centrally located along the apparatus;
   a heat exchanger comprising a plurality of heat transfer elements that are arranged around the core and between which blood from the core can move radially outward;
   an oxygenator comprising a plurality of gas exchange elements that are arranged around an entirety of the heat exchanger and between which blood from the heat exchanger can move radially outward before exiting the apparatus through the blood outlet, wherein at least some of the plurality of gas exchange elements of the oxygenator are wound directly onto and directly contact at least some of the plurality of heat transfer elements of the heat exchanger;
   wherein the core, heat exchanger and oxygenator are radially arranged within a housing having a peripheral wall radially positioned with respect to the oxygenator, a first end cap closing one open side of the peripheral wall and a second end cap closing another open side of the peripheral wall, the blood inlet being provided through the first end cap and the blood outlet being provided through the peripheral wall so as to be radially positioned to the core for controlling the flowpath from the core to the blood outlet.

2. The apparatus of claim 1, wherein the plurality of heat transfer elements are arranged concentrically about the core.

3. The apparatus of claim 1, wherein the plurality of gas exchange elements are arranged concentrically about the heat exchanger.

4. The apparatus of claim 1, wherein the core comprises a lumen having a longitudinal axis and a plurality of openings through which blood can move radially outward to the heat exchanger.

5. The apparatus of claim 4, wherein the blood can move axially along the lumen of the core until reaching the plurality of openings and then can move radially outward through the plurality of openings in a substantially transverse direction to the longitudinal axis.

6. The apparatus of claim 4, wherein blood can move radially outward from the core to the heat exchanger through substantially all of 360 degrees around the longitudinal axis.

7. The apparatus of claim 1, wherein the plurality of heat transfer elements include a lumen to which a fluid medium can be supplied in order to control the temperature of blood that can move between the plurality of heat transfer elements.

8. The apparatus of claim 7, wherein the plurality of heat transfer elements are arranged such that movement of the fluid medium through the plurality of heat transfer elements is substantially transverse to the radially outward direction that blood can move between the plurality of heat transfer elements.

9. The apparatus of claim 1, wherein the plurality of gas exchange elements comprise a lumen through which an oxygen-containing gas medium can be supplied in order to oxygenate blood that can move between the plurality of gas exchange elements.

10. The apparatus of claim 9, wherein the plurality of gas exchange elements are arranged such that the movement of the gas medium through the plurality of gas exchange elements is substantially transverse to the radially outward direction that blood can move between the plurality of gas exchange elements.

11. The apparatus of claim 1, further comprising a filter that is arranged around the oxygenator and through which blood moving radially outward from the oxygenator can move before exiting the apparatus through the outlet.

12. The apparatus of claim 1, wherein the core comprises a longitudinal axis and blood can move radially outward from the oxygenator through substantially all of 360 degrees around the longitudinal axis.

13. The apparatus of claim 1, further comprising a filter including filter media, wherein the filter media is wound in between the plurality of gas exchange elements.

14. The apparatus of claim 1, further comprising a filter through which blood can move before exiting the apparatus through the blood outlet.

15. The apparatus of claim 1, wherein the core comprises a longitudinal axis and blood can move radially outward from the heat exchanger through substantially all of 360 degrees around the longitudinal axis.

16. The apparatus of claim 1, further comprising a filter including filter media, wherein at least a portion of the filter media of the filter is located within the oxygenator.

17. An apparatus for oxygenating and controlling the temperature of blood in an extracorporeal circuit, the apparatus having a blood inlet and a blood outlet that is located radially outward from the blood inlet in order to define a flowpath through the apparatus, the apparatus comprising:
- a core that is substantially centrally located in the apparatus and to which blood from a patient can be supplied through the blood inlet, the blood inlet being centrally located along the apparatus;
- a heat exchanger comprising a plurality of heat transfer elements that are arranged around the core such that blood can move radially outward through the heat exchanger, each of the heat transfer elements terminating at opposing first and second end sections;
- an oxygenator comprising a plurality of gas exchange elements that are arranged around an entirety of the heat exchanger, each of the gas exchange elements terminating at opposing first and second end portions;
- a first potting structure encompassing the first end sections and the first end portions;
- a second potting structure encompassing the second end sections and the second end portions;
- wherein the first potting structure is separated from the second potting structure by a longitudinal spacing
- and further wherein the apparatus is configured such that relative to an entirety of the longitudinal spacing between the first and second potting structures, blood can move from the heat exchanger to the oxygenator without structural obstruction between the heat exchanger and the oxygenator and radially outward through the oxygenator before exiting the apparatus through the blood outlet.

18. The apparatus of claim 17, wherein the plurality of heat transfer elements are arranged concentrically about the core.

19. The apparatus of claim 17, wherein the plurality of gas exchange elements are arranged concentrically about the heat exchanger.

20. The apparatus of claim 17, wherein blood can move from the core to the heat exchanger without structural obstruction.

21. The apparatus of claim 17, wherein the core includes a lumen having a longitudinal axis and a plurality of openings through which blood can move radially outward to the heat exchanger.

22. The apparatus of claim 21, wherein the blood can move axially along the lumen of the core until reaching the plurality of openings and then can move radially outward through the plurality of openings in a substantially transverse direction to the longitudinal axis.

23. The apparatus of claim 22, wherein blood can move radially outward through substantially all of 360 degrees around the longitudinal axis of the core.

24. The apparatus of claim 17, wherein the plurality of heat transfer elements include a lumen through which a fluid medium can be supplied in order to control the temperature of blood that can move between the plurality of heat transfer elements.

25. The apparatus of claim 24, wherein the plurality of heat transfer elements are arranged such that movement of the fluid medium through the plurality of heat transfer elements is substantially transverse to the radially outward direction that blood can move between the plurality of heat transfer elements.

26. The apparatus of claim 17, wherein the plurality of gas exchange elements include a lumen through which an oxygen-containing gas medium can be supplied in order to oxygenate blood that can move between the plurality of gas exchange elements.

27. The apparatus of claim 26, wherein the plurality of gas exchange elements are arranged such that the movement of the gas medium through the plurality of gas exchange elements is substantially transverse to the radially outward direction that blood can move between the plurality of gas exchange elements.

28. The apparatus of claim 17, further comprising a filter that is concentrically arranged about the oxygenator and through which blood moving radially outward from the oxygenator can move before exiting the apparatus through the blood outlet.

29. The apparatus of claim 17, wherein the core comprises a longitudinal axis and blood can move radially outward from the oxygenator through substantially all of 360 degrees around the longitudinal axis.

30. The apparatus of claim 17, further comprising a housing that retains the core, the heat exchanger and the oxygenator.

31. The apparatus of claim 30 wherein the housing includes the blood inlet, which is in communication with the core.

32. The apparatus of claim 30, wherein the housing includes the blood outlet, which is located radially outward from the oxygenator.

33. The apparatus of claim 17, wherein the plurality of heat transfer elements are wound on the core.

34. The apparatus of claim 17, wherein the plurality of gas exchange elements are wound on the heat exchanger.

35. The apparatus of claim 34, further comprising a filter including filter media, wherein the filter media is wound in between the plurality of gas exchange elements.

36. The apparatus of claim 17, further comprising a filter through which blood can move before exiting the apparatus through the outlet.

37. The apparatus of claim 17, wherein the core comprises a longitudinal axis and blood can move radially outward from the heat exchanger through substantially all of 360 degrees around the longitudinal axis.

38. The apparatus of claim 17, further comprising a filter including filter media, wherein at least a portion of the filter media of the filter is located within the oxygenator.

39. An apparatus for oxygenating and controlling the temperature of blood in an extracorporeal circuit, the apparatus having a blood inlet and a blood outlet that is located radially outward from the blood inlet in order to define a flowpath through the apparatus, the apparatus comprising:
- a core that is substantially centrally located in the apparatus and to which blood from a patient can be supplied through the blood inlet, the blood inlet being centrally located along the apparatus;
- a heat exchanger comprising a plurality of heat transfer elements that are arranged around the core such that blood can move radially outward through the heat exchanger; and
- an oxygenator comprising a plurality of gas exchange elements that are arranged around an entirety of the heat exchanger such that blood can move from the heat exchanger to the oxygenator without structural obstruction between the heat exchanger and the oxygenator and radially outward through the oxygenator before exiting the apparatus through the blood outlet, wherein the core, heat exchanger and oxygenator are radially arranged within a housing having a peripheral wall radially positioned with respect to the oxygenator, a first end cap closing one open side of the peripheral wall and a second end cap closing another open side of the peripheral wall, the first end cap including a circular wall portion extending internally to a terminal end radially positioned between potted ends of the heat transfer elements and potted ends of the gas exchange elements so as to separate fluid flow to the heat exchanger and the oxygenator within a potted portion including ends of the heat transfer elements, ends of the gas exchange elements, and the terminal end of the circular wall.

40. The apparatus of claim 39, wherein the second end cap includes a circular wall portion extending internally to a radial position between opposite ends of the heat transfer elements and opposite ends of the gas exchange elements so as to separate the heat exchanger from the oxygenator.

* * * * *